(12) United States Patent
Hissong

(10) Patent No.: US 6,361,531 B1
(45) Date of Patent: Mar. 26, 2002

(54) FOCUSED ULTRASOUND ABLATION DEVICES HAVING MALLEABLE HANDLE SHAFTS AND METHODS OF USING THE SAME

(75) Inventor: James B. Hissong, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

(21) Appl. No.: 09/488,844

(22) Filed: Jan. 21, 2000

(51) Int. Cl.[7] ............................... A61B 18/04
(52) U.S. Cl. ..................... 606/27; 606/28; 606/78; 604/22; 600/437; 600/439; 600/446
(58) Field of Search ................. 600/437–446, 600/439; 606/32, 78, 14; 604/22

(56) References Cited

U.S. PATENT DOCUMENTS

| | | | |
|---|---|---|---|
| 3,990,452 A | | 11/1976 | Murry et al. |
| 4,508,122 A | * | 4/1985 | Gardineer et al. .......... 600/446 |
| 4,658,828 A | | 4/1987 | Dory |
| 4,807,633 A | | 2/1989 | Fry |
| 4,858,613 A | | 8/1989 | Fry et al. |
| 4,917,096 A | * | 4/1990 | Englehart et al. ........... 600/446 |
| 4,951,653 A | | 8/1990 | Fry et al. |
| 4,955,365 A | | 9/1990 | Fry et al. |
| RE33,590 E | | 5/1991 | Dory |
| 5,033,456 A | | 7/1991 | Pell et al. |
| 5,036,855 A | | 8/1991 | Fry et al. |
| 5,054,470 A | | 10/1991 | Fry et al. |
| 5,065,761 A | | 11/1991 | Pell |
| 5,080,101 A | | 1/1992 | Dory |
| 5,080,102 A | | 1/1992 | Dory |
| 5,117,832 A | | 6/1992 | Sanghvi et al. |
| 5,134,988 A | | 8/1992 | Pell et al. |
| 5,143,074 A | | 9/1992 | Dory |
| 5,150,711 A | | 9/1992 | Dory |
| 5,150,712 A | | 9/1992 | Dory |
| 5,158,070 A | | 10/1992 | Dory |
| 5,222,501 A | | 6/1993 | Ideker et al. |
| 5,267,954 A | | 12/1993 | Nita |
| 5,269,291 A | | 12/1993 | Carter |
| 5,269,297 A | | 12/1993 | Weng et al. |
| 5,295,484 A | | 3/1994 | Marcus et al. |
| 5,304,115 A | | 4/1994 | Pflueger et al. |

(List continued on next page.)

FOREIGN PATENT DOCUMENTS

WO    WO97/43970    11/1997

OTHER PUBLICATIONS

Company Press Release—FDA Clears First–of–its–Kind Device for Treatment of Sleep Disorder Affecting 20 Million Americans, 4pgs, Nov. 5, 1998.

(List continued on next page.)

Primary Examiner—Linda C. M. Dvorak
Assistant Examiner—A. Farah

(57) ABSTRACT

A focused ultrasound ablation device includes an ultrasound emitting member and a handle shaft having a distal end at which the ultrasound emitting member is disposed. The handle shaft is malleable to permit selective, manual shaping of the handle shaft to access a selected anatomical operative site from a remote location and/or to orient the ultrasound emitting member for contact with anatomical tissue at the selected operative site. A method of thermally ablating anatomical tissue includes the steps of manually shaping a malleable handle shaft to orient an active face of an ultrasound emitting member at a distal end of the shaft to contact anatomical tissue at a selected operative site, positioning the active face against the anatomical tissue at the operative site while a proximal end of the handle shaft is disposed at a remote location; emitting ultrasound energy from the ultrasound emitting member; focusing the ultrasound energy at one or more focusing zones within a target area in the tissue and located a predetermined distance in front of the active face and heating the tissue at the target area with the focused ultrasound energy to create a lesion.

29 Claims, 5 Drawing Sheets

U.S. PATENT DOCUMENTS

| | | |
|---|---|---|
| 5,312,328 A | 5/1994 | Nita et al. |
| 5,318,014 A | 6/1994 | Carter |
| 5,342,292 A | 8/1994 | Nita et al. |
| 5,354,258 A | 10/1994 | Dory |
| 5,380,274 A | 1/1995 | Nita |
| 5,391,197 A | 2/1995 | Burdette |
| 5,397,301 A | 3/1995 | Pflueger et al. |
| 5,409,002 A | 4/1995 | Pell |
| 5,417,672 A | 5/1995 | Nita et al. |
| 5,423,812 A | 6/1995 | Ellman et al. |
| 5,431,621 A | 7/1995 | Dory |
| 5,431,663 A | 7/1995 | Carter |
| 5,447,509 A | 9/1995 | Miller et al. |
| 5,456,662 A | 10/1995 | Edwards |
| 5,474,530 A | 12/1995 | Passafaro et al. |
| 5,492,126 A * | 2/1996 | Hennige et al. ............ 600/439 |
| 5,501,655 A | 3/1996 | Rolt et al. |
| 5,514,131 A | 5/1996 | Edwards |
| 5,520,188 A | 5/1996 | Hennige et al. |
| 5,542,917 A | 8/1996 | Nita et al. |
| 5,620,479 A | 4/1997 | Diederich |
| 5,624,439 A | 4/1997 | Edwards |
| 5,674,191 A | 10/1997 | Edwards |
| 5,676,692 A | 10/1997 | Sanghvi et al. |
| 5,707,349 A | 1/1998 | Edwards |
| 5,718,702 A | 2/1998 | Edwards |
| 5,720,719 A * | 2/1998 | Edwards et al. ............. 604/22 |
| 5,728,094 A | 3/1998 | Edwards |
| 5,730,719 A | 3/1998 | Edwards |
| 5,733,315 A | 3/1998 | Burdette et al. |
| 5,735,280 A | 4/1998 | Sherman et al. |
| 5,738,114 A | 4/1998 | Edwards |
| 5,743,870 A | 4/1998 | Edwards |
| 5,743,904 A | 4/1998 | Edwards |
| 5,746,224 A | 5/1998 | Edwards |
| 5,762,066 A * | 6/1998 | Law et al. .................. 600/439 |
| 5,800,379 A | 9/1998 | Edwards |
| 5,800,429 A | 9/1998 | Edwards |
| 5,800,482 A | 9/1998 | Pomeranz et al. |
| 5,807,308 A | 9/1998 | Edwards |
| 5,817,049 A | 10/1998 | Edwards |
| 5,823,197 A | 10/1998 | Edwards |
| 5,827,277 A | 10/1998 | Edwards |
| 5,843,077 A | 12/1998 | Edwards |
| 5,871,524 A | 2/1999 | Knowlton |
| 5,873,845 A | 2/1999 | Cline et al. |
| 5,873,902 A | 2/1999 | Sanghvi et al. |
| 5,879,349 A | 3/1999 | Edwards |
| 5,882,302 A | 3/1999 | Driscoll, Jr. et al. |
| 5,895,356 A | 4/1999 | Andrus et al. |
| 5,928,169 A | 7/1999 | Schätzle et al. |
| 5,938,608 A | 8/1999 | Bieger et al. |
| 5,984,881 A | 11/1999 | Ishibashi et al. |
| 5,984,882 A | 11/1999 | Rosenschein et al. |
| 6,007,499 A | 12/1999 | Martin et al. |
| 6,096,033 A | 8/2000 | Tu et al. |
| 6,135,971 A | 10/2000 | Hutchinson et al. |
| 6,174,280 B1 * | 1/2001 | Oneda et al. ................ 600/121 |
| 6,190,381 B1 * | 2/2001 | Olsen et al. .................. 606/32 |

OTHER PUBLICATIONS

Clinical Investigations—Radiofrequency Volumetric Tissue Reduction of the Palate in Subjects with Sleep–Disordered Breathing, Nelson B. Powell, MD; Robert W. Riley, DDS, MD; Robert J. Troell, MD; Kasey Li, MD; Marc B. Blumen, MD; Christian Guilleminault, MD, 12 pages, May 5, 1998.

Somnoplasty for Obstructive Sleep Apnea, 1 page, Jan. 6, 1999.

Somnoplasty For the Treatment of Snoring, 2 pgs, Jan. 6, 1999.

Sonablate Technology with HIFU, 2 pages, Feb. 17, 1999.

Focus Surgery, (McDonald & Company), 1 page, Feb. 23, 1999.

Laboratory and animal investigations—Radiofrequency Volumetric Reduction of the Tongue, Nelson B. Powell, MD; Robert W. Riley, MD; Robert J. Troell, MD; Marc B. Blumen, MD; Christian Guilleminault, MD, 8 pages, May 5, 1997.

* cited by examiner

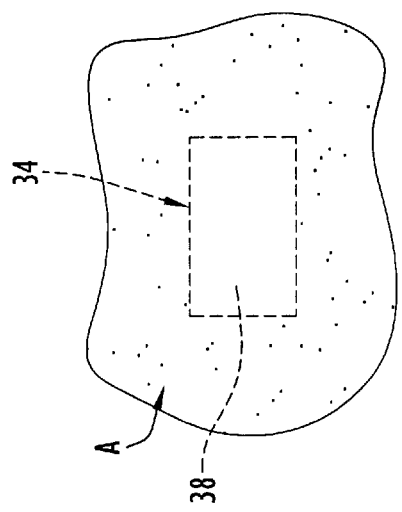
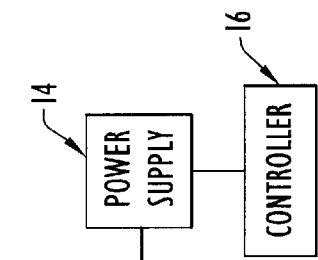
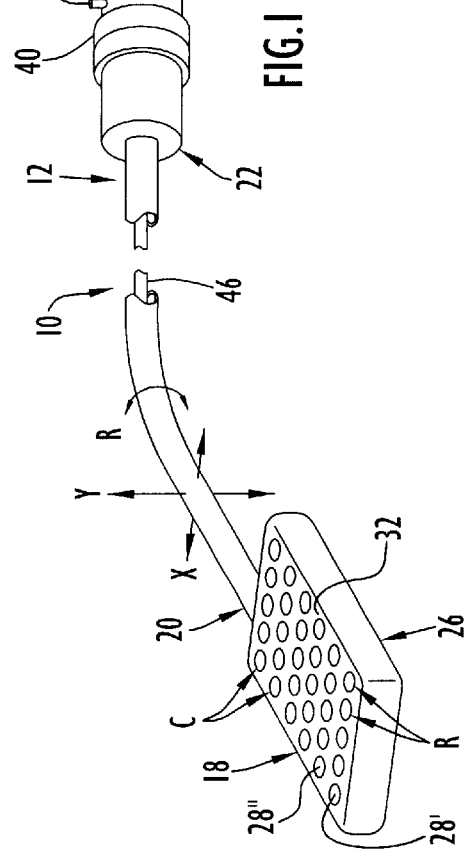
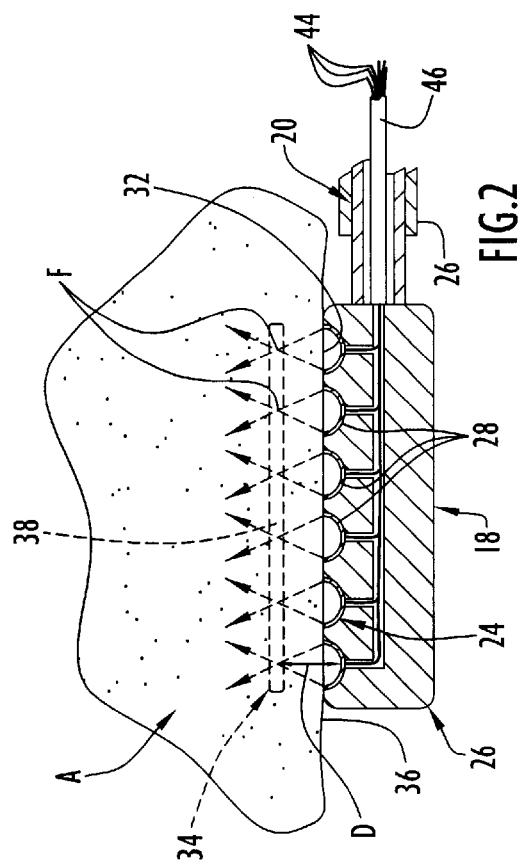

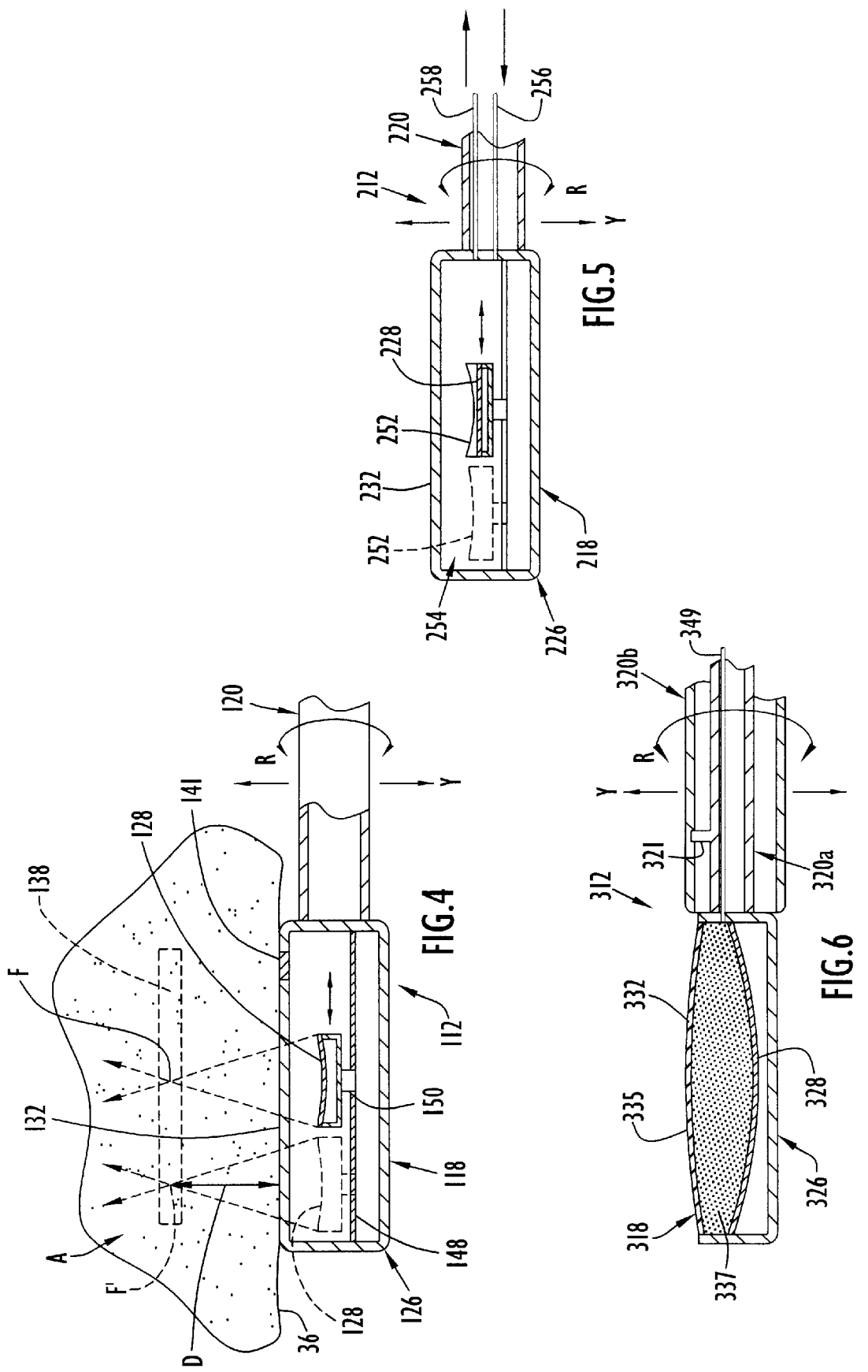

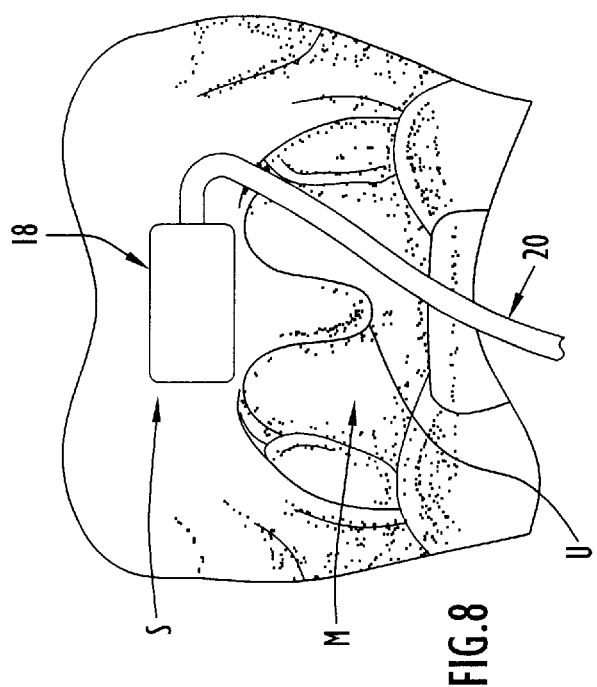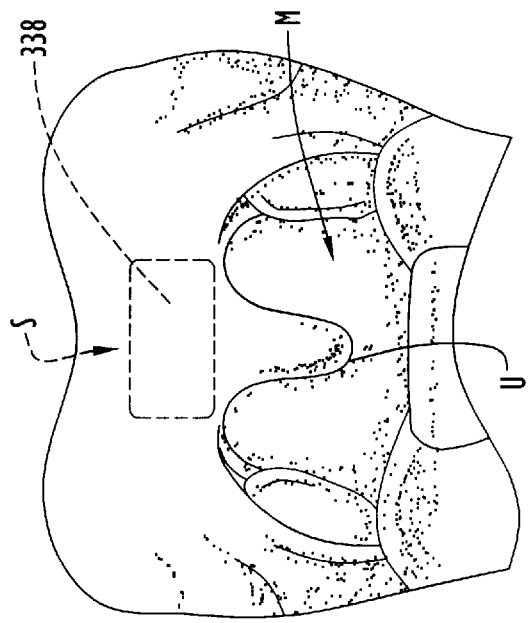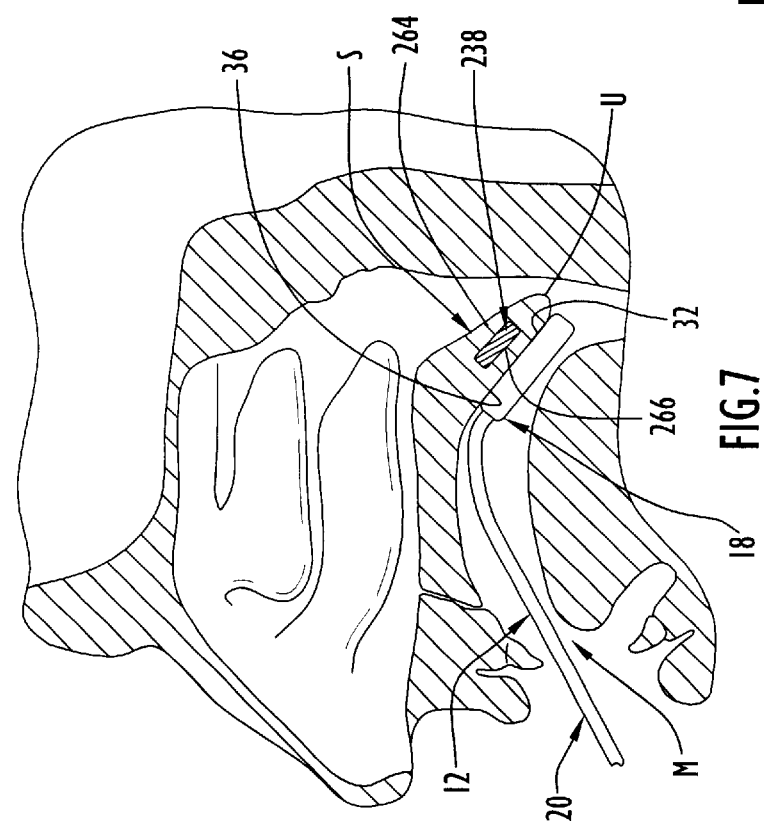

FOCUSED ULTRASOUND ABLATION DEVICES HAVING MALLEABLE HANDLE SHAFTS AND METHODS OF USING THE SAME

CROSS-REFERENCE TO RELATED PATENT APPLICATIONS

This application is related to co-pending U.S. patent applications entitled Methods of Soft Palate Reduction By Thermal Ablation Using High Intensity Focused Ultrasound Ser. No. 09/487,708, Methods of Tongue Reduction By Thermal Ablation Using High Intensity Focused Ultrasound Ser. No. 09/487,707, Methods of Tonsil Reduction By Thermal Ablation Using High Intensity Focused Ultrasound Ser. No. 09/487,709, Methods of Turbinate Or Other Soft Tissue Reduction By Thermal Ablation Using High Intensity Focused Ultrasound Ser. No. 09/487,706, Methods of Skin Rejuvenation By Thermal Stimulation Using High Intensity Focused Ultrasound Ser. No. 09/487,705, and Focused Ultrasound Ablation Devices Having Selectively Actuatable Ultrasound Emitting Elements and Methods of Using the Same Ser. No. 09/487,710, the disclosures of which are incorporated herein by reference.

BACKGROUND OF THE INVENTION

1. Field of the Invention

The present invention relates generally to the treatment of anatomical tissue with high intensity focused ultrasound energy and, more particularly, to hand-held focused ultrasound ablation devices having handle shafts used to position ultrasound emitting members adjacent tissue to be treated and to methods of using the same.

2. Brief Description of the Related Art

When high intensity ultrasound energy is applied to anatomical tissue, significant physiological effects may be produced in the anatomical tissue resulting from thermal and/or mechanical changes or effects in the tissue. Thermal effects include heating of the anatomical tissue; and, when the tissue is heated to a sufficiently high temperature, tissue damage such as coagulative necrosis is produced. In order to produce thermal effects in anatomical tissue, ultrasound emitting members having ultrasound emitting elements, such as transducers, have been used to emit ultrasound energy which is applied to anatomical tissue by positioning the ultrasound emitting members adjacent or in contact with the tissue or by coupling the ultrasound emitting members to the tissue via an acoustic coupling medium. By focusing the ultrasound energy at one or more specific focusing zones within the tissue, thermal effects can be confined to a defined location, region, volume or area, and such location, region, volume or area can be remote from the ultrasound emitting member.

With the use of high intensity focused ultrasound (HIFU), one or more focusing zones at or within a designated target location, region, volume or area within a larger mass, body or area of anatomical tissue can be subjected to high intensity ultrasound energy while tissue surrounding the target area is subjected to much lower intensity ultrasound energy. In this manner, tissue at the target area can be heated to a sufficiently high temperature so as to cause a desired thermal effect such as tissue damage, ablation, coagulation, denaturation, destruction or necrosis while tissue surrounding the target area is not heated to damaging temperatures and, therefore, is preserved. Heating of tissue at a target location, volume, region or area to an ablative temperature creates an ablative lesion in the tissue at the target location, volume, region or area that is desirable in the treatment of various medical conditions, disorders or diseases. For example, the lesion may remain as tissue having altered characteristics or may be naturally degraded and absorbed by the patient's body and thusly eliminated such that the remaining body, mass or area of tissue is of smaller volume or size due to the absence of the ablated tissue.

The use of high intensity focused ultrasound to eliminate tissue or to alter the characteristics of tissue at a target location, volume, region or area within a larger mass, body or area of anatomical tissue presents many advantages including minimization of trauma and pain for the patient, elimination of the need for a surgical incision, stitches and exposure of internal tissue, avoidance of damage to tissue other than that which is to be treated, altered or removed, lack of a harmful cumulative effect from the ultrasound energy on the surrounding non-target tissue, reduction in treatment costs, elimination of the need in many cases for general anesthesia, reduction of the risk of infection and other complications, avoidance of blood loss, and the ability for high intensity focused ultrasound procedures to be performed in non-hospital sites and/or on an out-patient basis.

Various devices and/or methods for treating anatomical tissue with ultrasound have been proposed as represented by U.S. Pat. No. Re. 33,590 to Dory, U.S. Pat. No. 3,990,452 to Murry et al, U.S. Pat. No. 4,658,828 to Dory, U.S. Pat. No. 4,807,633 to Fry, U.S. Pat. No. 4,858,613 to Fry et al, U.S. Pat. No. 4,951,653 to Fry et al, U.S. Pat. No. 4,955,365 to Fry et al, U.S. Pat. No. 5,033,456 to Pell et al, U.S. Pat. No. 5,036,855 to Fry et al, U.S. Pat. No. 5,054,470 to Fry et al, U.S. Pat. No. 5,065,761 to Pell, U.S. Pat. No. 5,080,101 to Dory, U.S. Pat. No. 5,080,102 to Dory, U.S. Pat. No. 5,117,832 to Sanghvi et al, U.S. Pat. No. 5,134,988 to Pell et al, U.S. Pat. No. 5,143,074 to Dory, U.S. Pat. No. 5,150,711 to Dory, U.S. Pat. No. 5,150,712 to Dory, U.S. Pat. No. 5,158,070 to Dory, U.S. Pat. No. 5,222,501 to Ideker et al, U.S. Pat. No. 5,267,954 to Nita, U.S. Pat. No. 5,269,291 to Carter, U.S. Pat. No. 5,269,297 to Weng et al, U.S. Pat. No. 5,295,484 to Marcus et al, U.S. Pat. No. 5,304,115 to Pflueger et al, U.S. Pat. No. 5,312,328 to Nita et al, U.S. Pat. No. 5,318,014 to Carter, U.S. Pat. No. 5,342,292 to Nita et al, U.S. Pat. No. 5,354,258 to Dory, U.S. Pat. No. 5,380,274 to Nita, U.S. Pat. No. 5,391,197 to Burdette et al, U.S. Pat. No. 5,397,301 to Pflueger et al, U.S. Pat. No. 5,409,002 to Pell, U.S. Pat. No. 5,417,672 to Nita et al, U.S. Pat. No. 5,431,621 to Dory, U.S. Pat. No. 5,431,663 to Carter, U.S. Pat. No. 5,447,509 to Mills et al, U.S. Pat. No. 5,474,530 to Passafaro et al, U.S. Pat. No. 5,492,126 to Hennige et al, U.S. Pat. No. 5,501,655 to Rolt et al, U.S. Pat. No. 5,520,188 to Hennige et al, U.S. Pat. No. 5,542,917 to Nita et al, U.S. Pat. No. 5,620,479 to Diederich, U.S. Pat. No. 5,676,692 to Sanghvi et al, U.S. Pat. No. 5,728,094 to Edwards, U.S. Pat. No. 5,730,719 to Edwards, U.S. Pat. No. 5,733,315 to Burdette et al, U.S. Pat. No. 5,735,280 to Sherman et al, U.S. Pat. No. 5,738,114 to Edwards, U.S. Pat. No. 5,746,224 to Edwards, U.S. Pat. No. 5,762,066 to Law et al, U.S. Pat. No. 5,800,379 to Edwards, U.S. Pat. No. 5,800,429 to Edwards, U.S. Pat. No. 5,800,482 to Pomeranz et al, U.S. Pat. No. 5,807,308 to Edwards, U.S. Pat. No. 5,817,049 to Edwards, U.S. Pat. No. 5,823,197 to Edwards, U.S. Pat. No. 5,827,277 to Edwards, U.S. Pat. No. 5,843,077 to Edwards, U.S. Pat. No. 5,871,524 to Knowlton, U.S. Pat. No. 5,873,845 to Cline et al, U.S. Pat. No. 5,873,902 to Sanghvi et al, U.S. Pat. No. 5,879,349 to Edwards, U.S. Pat. No. 5,882,302 to Driscoll, Jr. et al, U.S. Pat. No. 5,895,356 to Andrus et al, U.S. Pat. No. 5,928,169 to Schätzle et al and U.S. Pat. No. 5,938,608 to Bieger et al.

In particular, focused ultrasound ablation devices used to thermally damage, ablate, coagulate, denature, cauterize, necrotize or destroy a target volume of tissue are exemplified by U.S. Pat. No. Re. 33,590 to Dory, U.S. Pat. No. 4,658,828 to Dory, U.S. Pat. No. 4,807,633 to Fry, U.S. Pat. No. 4,858,613 to Fry et al, U.S. Pat. No. 4,951,653 to Fry et al, U.S. Pat. No. 4,955,365 to Fry et al, U.S. Pat. No. 5,036,855 to Fry et al, U.S. Pat. No. 5,054,470 to Fry et al, U.S. Pat. No. 5,080,101 to Dory, U.S. Pat. No. 5,080,102 to Dory, U.S. Pat. No. 5,117,832 to Sanghvi et al, U.S. Pat. No. 5,143,074 to Dory, U.S. Pat. No. 5,150,71 to Dory, U.S. Pat. No. 5,150,712 to Dory, U.S. Pat. No. 5,295,484 to Marcus et al, U.S. Pat. No. 5,354,258 to Dory, U.S. Pat. No. 5,391,197 to Burdette et al, U.S. Pat. No. 5,431,621 to Dory, U.S. Pat. No. 5,492,126 to Hennige et al, U.S. Pat. No. 5,501,655 to Rolt et al, U.S. Pat. No. 5,520,188 to Hennige et al, U.S. Pat. No. 5,676,692 to Sanghvi et al, U.S. Pat. No. 5,733,315 to Burdette et al, U.S. Pat. No. 5,762,066 to Law et al, U.S. Pat. No. 5,871,524 to Knowlton, U.S. Pat. No. 5,873,845 to Cline et al, U.S. Pat. No. 5,873,902 to Sanghvi et al, U.S. Pat. No. 5,882,302 to Driscoll, Jr. et al, U.S. Pat. No. 5,895,356 to Andrus et al, U.S. Pat. No. 5,928,169 to Schätzle et al and U.S. Pat. No. 5,938,608 to Bieger et al. The focused ultrasound ablation devices are used to ablate various areas in or on the bodies of patients including the brain, prostate, heart, urethra, blood vessels, deep seated tissue and tumors, liver, kidney, skin, breast, stomach and pancreas.

Prior focused ultrasound ablation devices have been designed to access anatomical sites at which ultrasound emitting members of the devices must be placed in order to ablate designated target areas. For example, some prior focused ultrasound ablation devices, of which U.S. Pat. No. Re. 33,590, U.S. Pat. Nos. 4,658,828, 5,080,101, 5,080,102, 5,150,712 and 5,431,621 are representative, are designed as structure for being positioned over and/or attached to a patient's skull. As another example, some prior focused ultrasound ablation devices have been designed as part of a table or support on which a patient is disposed or as structure positioned over such a table or support as represented by U.S. Pat. Nos. 4,951,653, 5,054,470 and 5,873,845. As a further example, U.S. Pat. Nos. 5,295,484, 5,391,197, 5,492,126, 5,676,692, 5,762,066 and 5,895,356 are illustrative of focused ultrasound ablation devices having ultrasound emitting members carried in, on or coupled to flexible shafts, probes or catheters insertable in anatomical lumens, with the shafts, probes or catheters naturally conforming to the configurations of the anatomical lumens. U.S. Pat. Nos. 5,150,711, 5,143,074, 5,354,258 and 5,501,655 are representative of focused ultrasound ablation devices having portions thereof placed against or in contact with patients' bodies.

Ablation of anatomical tissue of the head and/or neck in order to reduce or eliminate such tissue in the treatment of various airway related disorders has also been proposed as illustrated by U.S. Pat. No. 5,423,812 to Ellman et al, U.S. Pat. Nos. 5,456,662, 5,514,131, 5,624,439, 5,674,191, 5,707,349, 5,718,702, 5,728,094, 5,730,719, 5,738,114, 5,743,870, 5,743,904, 5,746,224, 5,800,379, 5,800,429, 5,807,308, 5,817,049, 5,823,197, 5,827,277, 5,843,077 and 5,879,349 to Edwards and WO 97/43970. The areas ablated include the soft palate, uvula, tongue, tonsils, adenoids and turbinates. U.S. Pat. No. 5,423,812 relates to electrosurgical stripping of tissue. U.S. Pat. Nos. 5,456,662, 5,514,131, 5,624,439, 5,674,191, 5,707,349, 5,718,702, 5,728,094, 5,730,719, 5,738,114, 5,743,870, 5,743,904, 5,746,224, 5,800,379, 5,800,429, 5,807,308, 5,817,049, 5,823,197, 5,827,277, 5,843,077, 5,879,349 and WO97/43970 disclose RF ablation using tissue penetrating electrodes. U.S. Pat. Nos. 5,707,349, 5,728,094, 5,730,719, 5,738,114, 5,746, 224, 5,800,379, 5,800,429, 5,807,308, 5,817,049, 5,823,197, 5,827,277, 5,843,077 and 5,879,349 refer to ultrasound as a possible source of ablative energy.

Ablation devices used to treat anatomical tissue accessible via the nasal and/or oral cavities of patients are typically hand-held devices manually manipulated by a surgeon or other operator to position a portion or portions of the devices adjacent or in contact with anatomical tissue of the patients. U.S. Pat. Nos. 5,423,812, 5,456,662, 5,514,131, 5,624,439, 5,674,191, 5,707,349, 5,718,702, 5,728,094, 5,730,719, 5,738,114, 5,743,870, 5743,904, 5,800,379, 5,807,308, 5,817,049 and 5,879,349 and WO97/43970 disclose hand-held RF ablation devices having elongate shafts, arms, probes or catheters extending from handles and carrying tissue penetrating electrodes. U.S. Pat. Nos. 5,707,349, 5,728,094, 5,730,719, 5,738,114, 5,800,379, 5,807,308, 5,817,049 and 5,879,349 disclose catheters that may be malleable in order to conform to the surface of the tongue. WO97/43970 discloses a catheter having a malleable tip.

The pending patent applications incorporated herein by reference and entitled Methods of Soft Palate Reduction By Thermal Ablation Using High Intensity Focused Ultrasound, Methods of Tongue Reduction By Thermal Ablation Using High Intensity Focused Ultrasound, Methods of Tonsil Reduction By Thermal Ablation Using High Intensity Focused Ultrasound, Methods of Turbinate Or Other Soft Tissue Reduction By Thermal Ablation Using High Intensity Focused Ultrasound, Methods of Skin Rejuvenation By Thermal Stimulation Using High Intensity Focused Ultrasound and Focused Ultrasound Ablation Devices Having Selectively Actuatable Ultrasound Emitting Elements and Methods of Using the Same disclose focused ultrasound ablation devices including ultrasound emitting members carried by elongate handle shafts respectively coupled to handles used by surgeons or other operators to position active faces of the ultrasound emitting members adjacent or in contact with anatomical tissue or structures to effect ablation at various designated target areas in the tissue or structures.

It would be desirable for the configuration of the handle shafts to be selectively adjustable to access various anatomical tissues or structures from externally of patients' bodies and/or to orient the active faces in accordance with the locations of the designated target areas. It would be desirable for an individual handle shaft to be capable of assuming various selected configurations while the handle thereof remains in an operative position or orientation for optimum grasping by the surgeon or other operator. In this manner, the handle could be grasped by the surgeon or other operator in the same way each time the focused ultrasound ablation device was used, while the handle shaft could be disposed in different selected configurations relative to the handle for each use. It would be desirable for selective adjustment of the configurations of the handle shafts to be obtainable with minimal effort and time expended by the surgeon or other operator and without complex operational steps. It would also be desirable for the handle shafts, once adjusted to selected configurations, to effectively maintain the selected configurations without further intervention by the surgeon or other operator so that the active faces remain properly positioned during the ablation procedures.

Accordingly, the need exists for a hand-held focused ultrasound ablation device having a handle shaft that is selectively adjustable, with minimal time and effort by a surgeon or other operator, in order to adapt the handle shaft for accessing anatomical tissue or structure of a patient from a remote location, typically external of the patient's body, and/or to properly orient an active face disposed at a distal end of the shaft so that the active face may be positioned at a desired location on the tissue or structure. A need exists for a focused ultrasound ablation device having a malleable handle shaft capable of being selectively shaped to avoid anatomical obstacles when introduced in an anatomical passageway used to access an internal operative site. The need further exists for a focused ultrasound ablation device having a selectively adjustable handle shaft by which a single focused ultrasound ablation device can be adapted to effect ablation at various anatomical areas including, for example, the soft palate, tongue, tonsils, turbinates or other soft tissue and skin. There is also a need for a focused ultrasound ablation device having a malleable handle shaft by which an active face of the device can be selectively oriented horizontally, vertically, transversely and/or at various angles, thereby increasing the areas of potential use for the focused ultrasound ablation device. An additional need exists for a focused ultrasound ablation device having a malleable handle shaft which, upon being manually placed in a selected configuration by a surgeon or other operator, maintains the selected configuration without further intervention by the surgeon or other operator.

SUMMARY OF THE INVENTION

Accordingly, it is a primary object of the present invention to overcome the various disadvantages of prior focused ultrasound ablation devices.

It is also an object of the present invention to provide a hand-held focused ultrasound ablation device having an ultrasound emitting member at a distal end of a malleable handle shaft by which the orientation of the ultrasound emitting member can be selectively adjusted.

Another object of the present invention is to provide a hand-held focused ultrasound ablation device having an ultrasound emitting member at a distal end of a malleable handle shaft allowing the configuration of the handle shaft to be selectively manually adjusted for accommodation in an anatomical passageway through which the handle shaft is to be introduced, from external of a patient's body, in order to position the ultrasound emitting member at an operative site in the patient's body.

A further object of the present invention is to selectively shape a malleable handle shaft, coupled to an ultrasound emitting member, so that an active face of the ultrasound emitting member is positioned at a desired location on anatomical tissue within which an ablative lesion is to be formed with ultrasound energy emitted by the ultrasound emitting member.

An additional object of the present invention is to facilitate the performance of high intensity focused ultrasound ablation procedures in various anatomical areas with the use of a single focused ultrasound ablation device.

It is also an object of the present invention to provide a focused ultrasound ablation device having a malleable handle shaft capable of axial and/or torsional adjustment.

Yet another object of the present invention is to selectively shape a malleable handle shaft of a focused ultrasound ablation device to assume various different configurations for different procedural uses while a handle coupled to the shaft is in the same orientation for each procedural use.

The present invention also has as an object to permit selective adjustment of the configuration of a handle shaft of a focused ultrasound ablation device so that an active face of an ultrasound emitting member coupled to the handle shaft can be selectively oriented to assume various vertical, horizontal and transverse positions, or combinations thereof, at various angles.

Some of the advantages of the present invention are that the need for mechanical steering devices is eliminated, the handle shaft is not limp and shapeless but, rather, has sufficient rigidity thereto to facilitate handling and use, the handle shaft, once placed in a selected configuration, maintains the selected configuration without further interaction therewith, the handle shaft can be shaped to assume configurations corresponding to the configurations of various anatomical passageways such as the oral cavity and nasal passageways, the handle shaft can be configured to avoid anatomical tissues or structures in the anatomical passageways through which the handle shaft is to be introduced in order to access operative sites from remote locations, such as externally of patients' bodies, tissues or structures in the anatomical passageways may not have to be retracted, manipulated or otherwise interfered with since the handle shaft is capable of being configured to avoid or circumvent such tissues or structures, the handle shaft has sufficient rigidity to allow the active face to be held against a tissue surface via a handle proximally coupled to the handle shaft, the configurations of the handle shaft can be adjusted prior to or during use with minimal effort and time expended by the surgeon or other operator and without the need for highly specialized skill and expertise, the configuration of the handle shaft can be adjusted without damage to mechanical components within the handle shaft, the force needed to shape the handle shaft can be minimized, the active face can be made to assume virtually any desired angle, the handle can be grasped and held by surgeons or other operators while in the same orientation or position for consistency of use even though the handle shaft and/or active face may be in various different orientations or configurations, the focused ultrasound ablation device does not have to be customized for use in a specific area of the body, and the focused ultrasound ablation device can be provided ag a standardized instrument capable of being used in or on a wide variety of areas of patients' bodies.

These and other objects, advantages and benefits are realized with the present invention as generally characterized in a focused ultrasound ablation device comprising an ultrasound emitting member, an elongate handle shaft having a distal end at which the ultrasound emitting member is disposed and a handle coupled to a proximal end of the handle shaft. The ultrasound emitting member emits ultrasound energy and causes the emitted ultrasound energy to be focused in front of an active face of the ultrasound emitting member. The handle shaft is malleable to permit longitudinal and/or torsional adjustment or shaping of the handle shaft for accommodation in an anatomical passageway through which the handle shaft is to be introduced to position the ultrasound emitting member at a selected operative site and/or to selectively orient the active face to contact anatomical tissue at the operative site. Via adjustment of the handle shaft, the active face can be oriented to face upwardly, downwardly, laterally or forwardly of the ablation device or at various positions therebetween. By adjusting the handle shaft, ultrasound energy is emitted from the ultrasound emitting member in a desired direction relative to the handle shaft and/or the handle so that the ultrasound energy is focused at a desired target area in the anatomical tissue.

A method of thermally ablating anatomical tissue of a patient is generally characterized by the steps of manually shaping a malleable handle shaft of a focused ultrasound ablation device so an active face of an ultrasound emitting member carried at a distal end of the handle shaft is oriented to contact anatomical tissue at an operative site, positioning the active face against the tissue at the operative site, emitting ultrasound energy from the ultrasound emitting member, focusing the ultrasound energy at a focusing zone contained in target area within the anatomical tissue and located a predetermined distance in front of the active face, and heating the tissue at the target area with the focused ultrasound energy to form a lesion.

Other objects and advantages of the present invention will become apparent from the following description of the preferred embodiments taken in conjunction with the accompanying drawings, wherein marked parts in each of the several figures are identified, by the same reference characters.

BRIEF DESCRIPTION OF THE DRAWINGS

FIG. 1 is a broken perspective view, partly schematic, illustrating a focused ultrasound ablation assembly incorporating a focused ultrasound ablation device according to the present invention.

FIG. 2 is a broken side view, partly in section, of an ultrasound emitting member of the focused ultrasound ablation device and depicting focusing of ultrasound energy in anatomical tissue to form a lesion.

FIG. 3 is a broken bottom view of the tissue illustrating the surface configuration of the lesion.

FIG. 4 is a broken side view, partly in section, of an alternative focused ultrasound ablation device according to the present invention.

FIG. 5 is a broken side view, partly in section, of another alternative focused ultrasound ablation device according to the present invention.

FIG. 6 is a broken side view, partly in section, of a further alternative focused ultrasound ablation device according to the present invention.

FIG. 7 is a broken side view, partly in section, illustrating a handle shaft of the focused ultrasound ablation device of FIG. 1 adjusted to position an active face of the ultrasound emitting member against the soft palate of a patient to create an internal lesion.

FIG. 8 is a broken anterior view illustrating the handle shaft of the focused ultrasound ablation device of FIG. 1 alternatively adjusted to position the active face of the ultrasound emitting member transversely against the soft palate of a patient to create an alternative internal lesion.

FIG. 9 is a broken anterior view illustrating the alternative lesion of FIG. 8 created in the soft palate.

DESCRIPTION OF THE PREFERRED EMBODIMENTS

Figure 11:
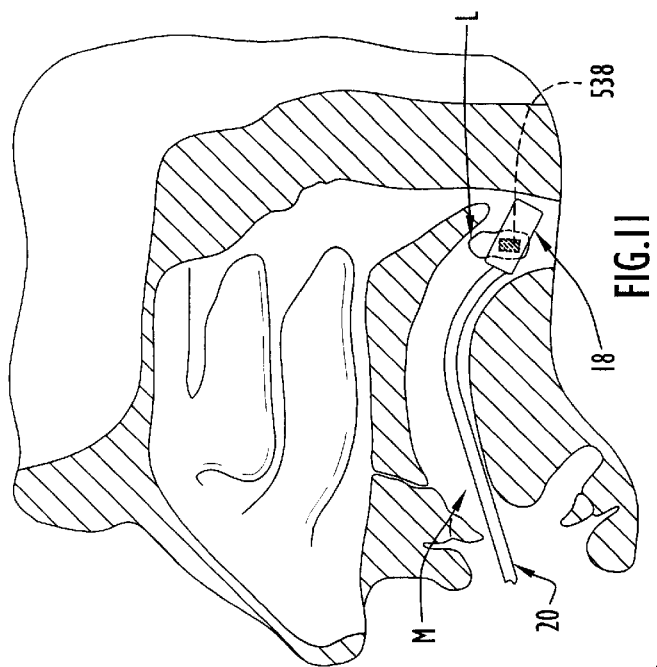
FIG. 11 is a broken side view, partly in section, illustrating the handle shaft of the focused ultrasound ablation device of FIG. 1 adjusted to position the active face of the ultrasound emitting member against a tonsil of a patient to create an internal lesion.

A high intensity focused ultrasound ablation assembly or system 10 incorporating a focused ultrasound ablation device 12 according to the present invention is illustrated in FIG. 1. The high intensity focused ultrasound ablation assembly 10 includes focused ultrasound ablation device 12, a power supply 14 and a controller 16. The focused ultrasound ablation device 12 includes a focused ultrasound emitting member 18, an elongate handle shaft or body 20 having a distal end at which the ultrasound emitting member is disposed and a handle or handpiece 22 coupled to a proximal end of the handle shaft 20. As shown in FIG. 2, the ultrasound emitting member includes a transducer 24 carried by or within a housing, carrier or case 26. The transducer, which includes one or more individual ultrasound emitting elements or transducer elements, is capable of generating and emitting ultrasound energy in response to being supplied with electrical power from power supply 14. In the case of ultrasound emitting member 18, the transducer includes a plurality of individual ultrasound emitting elements or transducer elements 28, each including a piezoelectric element that vibrates to produce ultrasound energy when an electrical current or signal is supplied thereto. The transducer elements 28 have a focusing configuration or geometry that results in the ultrasound energy produced thereby being focused a fixed distance from the ultrasound emitting member. The transducer elements 28 have a partial spherical or concave configuration causing the ultrasound energy generated thereby to be focused, as shown by arrows in FIG. 2, at focusing zones F, respectively.

The transducer elements 28 are arranged in an array on or in housing 26; and, therefore, the transducer 24 may be considered a multi-array transducer. In the case of ultrasound emitting member 18, the transducer elements are arranged in a planar array of five rows R and six columns C, although the transducer elements can be arranged in any number of rows and columns depending on the number of transducer elements, provided in the ultrasound emitting member. In the case of focused ultrasound emitting member 18, each row R has an equal number of transducer elements, and each column C has an equal number of transducer elements. It should be appreciated that any number of transducer elements can be provided in each row and column and that the number of transducer elements provided in each row and column can be the same or different.

The transducer elements 28 can be referenced by their location in the array. For example, the transducer element 28' in the first row, first column can be designated transducer element R1C1, the transducer element 28" in the first row, second column can be designated transducer element R1C2 and so on. The transducer elements of each row are disposed close to one another, and the transducer elements of each column are disposed close to one another such that there is minimal space between adjacent transducer elements. As explained further below, the transducer elements 28 are selectively, independently actuatable to selectively emit or not emit ultrasound energy.

The transducer elements 28 can be designed in various ways as known in the art. In the case of transducer 24, the transducer elements each comprise a piezoelectric element formed by a layer of piezoelectric material carried by housing 26. The piezoelectric elements are recessed from a planar external surface 32 of housing 26. The piezoelectric elements are curved in a direction inwardly of surface 32 such that ultrasound energy generated by the piezoelectric elements is emitted from focused ultrasound emitting member 18 in a direction perpendicular to surface 32 for focusing at the focusing zones F, which are spaced outwardly of surface 32. Accordingly, surface 32 is an active surface or face of the ultrasound emitting member which, when positioned externally on, adjacent or in contact with a mass, body or area of anatomical tissue A, results in the ultrasound energy emitted by the transducer being focused at zones F, which will be disposed within the anatomical tissue A as shown in FIG. 2. When the ultrasound emitting member is positioned on, against or adjacent the tissue A at a location aligned with a designated target area 34 within the tissue A, the focusing zones will be disposed at or within the target area as shown in FIG. 2.

Each focusing zone F consists of a single point or a plurality of points forming a zone at which the ultrasound energy is focused. Each focusing zone is in line with a central axis of the corresponding transducer element. Each focusing zone is disposed a fixed predetermined distance D from a plane containing the active face 32, the distance D for each focusing zone being perpendicular or normal to the active face 32. Therefore, the focusing zones F will also be disposed a predetermined perpendicular distance or a calculable or determinable perpendicular distance from an external tissue surface 36 of tissue A with which the active face 32 is placed in contact or adjacent thereto. Where the active face 32 is placed in contact with the external tissue surface 36, the perpendicular distance that zones F are disposed from external tissue surface 36 will be the same as the predetermined distance D as shown in FIG. 2. Where the active face 32 is not placed in contact with the external tissue surface 36 but, rather, is spaced from the external tissue surface 36 by a known amount, for example, the perpendicular distance that zones F are disposed from the external tissue surface will correspond to distance D minus the distance that the active face 32 is spaced from the external tissue surface 36. Where the active face 32 is spaced from the external tissue surface 36, an acoustic coupling medium can be disposed between the external tissue surface 36 and the member 18 as explained further below.

Since the ultrasound is focused at zones F, the ultrasound is of greater or higher intensity at focusing zones F and is thusly focused or concentrated at the focusing zones F, causing tissue A at the focusing zones F to be heated to an ablative temperature. When all of the transducer elements 28 are actuated, as shown in FIG. 2, heating of tissue A will occur at a focusing zone F for each transducer element. Since the transducer elements are disposed close to one another, the areas of tissue between the focusing zones are also heated to an ablative temperature due to thermal conduction causing the dispersal or spread of heat from the focusing zones. Accordingly, a discrete, definitive lesion 38 is formed in the tissue while the temperature of the tissue surrounding the lesion remains below damaging levels such that the surrounding tissue is undamaged and preserved. When all of the transducer elements 28 are actuated, a lesion of specific configuration and size is created within the body, mass or area of anatomical tissue A for the transducer 24 in accordance with the intensity level of the emitted ultrasound energy and the duration or time of ultrasound energy delivery to the tissue. Accordingly, a lesion having a specific length, width and depth is formed in the tissue. FIGS. 2 and 3 illustrate the lesion 38 formed in tissue A when all of the transducer elements are actuated. The lesion 38 has a generally rectangular surface configuration with a predetermined length and width dictated by the configuration of the array and a predetermined depth dictated by the length of the focusing zones. When the ultrasound emitting member 18 is positioned on, against or adjacent the tissue A at a location aligned with a designated target or lesion area 34 in the tissue, the lesion 38 will be formed at or coincide with the target area as shown in FIGS. 2 and 3.

The housing 26 can have various external configurations and sizes in accordance with the size, configuration and design of the transducer and the array in which the transducer elements are arranged including rectangular, square, circular, curved and cylindrical or tubular configurations. In the case of ultrasound emitting member 18, the housing 26 has a generally rectangular external configuration with rounded or blunt corners and/or edges to avoid damage to anatomical tissue. It should be appreciated that the transducer elements 28 can be disposed within the housing with the ultrasound energy generated by the transducer elements being transmitted or emitted through or from a wall of the housing, such wall being made of material through which ultrasound energy can pass and defining the active face for the ultrasound emitting member. Of course, a surface of the transducer can itself define the active face for the ultrasound emitting member.

The active face for ultrasound emitting member 18 is parallel to a longitudinal axis of member 18 so that the predetermined distance for zones F beyond the active face and the external tissue surface is perpendicular to the longitudinal axis. It should be appreciated that, depending on the design of the ultrasound emitting member, the predetermined distances for the focusing zones beyond the active face and the external tissue surface can be perpendicular to the active face but non-perpendicular to the longitudinal axis. The active face may be rigid or flexible or deformable depending on procedural use. The active face and/or the transducer may be designed to conform to the shape of the tissue surface against which the active face is placed. Of course, where soft tissue is being ablated, the soft tissue may conform to the shape of the active face and/or the transducer where the active face and/or the transducer is/are more rigid than the tissue.

The handle shaft 20 comprises a hollow or tubular malleable shaft member of sufficient length to position the ultrasound emitting member 18 at various operative sites in or on the body of a patient while the handle 22 is maintained at a remote location, typically externally of the patient's body. Malleability of the handle shaft 20 may be obtained, for example, by forming the shaft member of a malleable material including malleable metals such as aluminum, brass, alloys of steel and heat treated steel. Another exemplary manner in which malleability of the handle shaft 20 may be obtained is by forming the shaft member of a plurality of annular segments flexibly connected to one another in series and covered by a flexible or compliant sheath 26, shown in FIG. 2, such as a sheath made of stretchable elastic or rubber. An additional exemplary way in which malleability may be imparted to the handle shaft 20 is by forming the shaft member as a spiral winding. For example, the shaft member may have a spiral cut therein covered by one or more strips of material spirally wound over the shaft member. Of course, depending on the design of the handle shaft, the shaft member may be disposed in a sheath to present a smooth external surface. Depending on the materials and/or structure used to impart malleability to the handle shaft, the handle shaft will be axially or longitudinally and/or torsionally adjustable as discussed further below.

The handle 22 has a forward end coupled to the proximal end of handle shaft 20 and has a rearward end. The handle 22 preferably has a configuration to facilitate grasping by a surgeon or other operator. In the case of focused ultrasound ablation device 12, the handle 22 has a cylindrical body with raised, external annular segments 40. The segments 40 are longitudinally spaced from one another, and one or more controls or switches 42, such as push button controls or switches, may be disposed on handle 22 between spaced segments 40. The one or more controls or switches 42, where provided, may be used to effect operation of the focused ultrasound ablation device. It should be appreciated that the handle can be provided without controls or switches in which case operation of the focused ultrasound ablation device may be effected by one or more controls or switches located on the power supply, the controller and/or a dedicated structure such as a foot pedal. Where the one or more controls or switches are provided on the handle, as illustrated for focused ultrasound ablation device 12, the one or more controls or switches is/are desirably placed at a location on the handle amenable to convenient operation thereof by the hand of the surgeon or other operator grasping the handle. As shown in FIG. 1, the push button controls or switches 42 are accessible and operable by a finger of the hand grasping the handle 22 for one-handed operation of ablation device 12. In the case of handle 22, the switches are longitudinally aligned with one another along a line that is parallel to a longitudinal axis of the handle. When the handle is grasped so as to be optimally positioned or oriented for use and operation of the ablation device, the handle will be in a preferred or operative position or orientation. In the operative position, the handle is in a predetermined orientation with the switches disposed at the top of the handle for optimally convenient grasping and use by an operator as shown in FIG. 1.

The proximal end of handle shaft 20 is coupled with handle 22 at the forward end thereof and, in particular, at a forward wall of the handle. The proximal end of handle shaft 20 maybe disposed on or within the forward wall or may extend through the forward wall to be disposed within the handle 22. With the proximal end of the handle shaft thusly coupled to the handle, the longitudinal axis of the handle is coaxially aligned with the longitudinal axis of the handle shaft at the proximal end thereof. The shaft and the handle are preferably made of a material or materials that does/do not transmit ultrasound energy to the surgeon or other operator.

The handle shaft 20, being malleable, is capable of being manually moved or shaped longitudinally and/or torsionally. In this manner, the handle shaft 20 is selectively adjustable to be made to assume a straight longitudinal configuration, various non-straight longitudinal configurations, a non-torsionally rotated configuration and/or various torsionally rotated configurations. As shown by arrow X in FIG. 1, which shows handle shaft 20 capable of both longitudinal and torsional adjustment, one or more length segments or portions of the handle shaft 20 is/are capable of being moved in a lateral or horizontal direction to shape the handle shaft longitudinally. In particular, one or more length segments or portions of the handle shaft is/are capable of being moved to the left and/or the right in the horizontal direction as shown by arrow X. As shown by arrow Y in FIG. 1, one or more length segments or portions of the handle shaft 20 is/are capable of being moved in a vertical direction to shape the handle shaft longitudinally. In particular, one or more length segments or portions of the handle shaft is/are capable of being moved upwardly and/or downwardly in the vertical direction as shown by arrow Y. One or more length segments or portions of the handle shaft 20 is/are capable of being moved in various combined horizontal and vertical directions to shape the handle shaft longitudinally. For example, one or more length segments or portions of the handle shaft can be moved toward the left or the right in the horizontal direction as well as upwardly or downwardly in the vertical direction to obtain longitudinal shaping of the handle shaft at various angles between the horizontal and vertical. As shown by arrow R in FIG. 1, one or more length segments or portions of the handle shaft 20 is/are capable of being moved in a torsional or rotational direction to shape or twist the handle shaft torsionally. In particular, one or more length segments or portions of the handle shaft is/are capable of being moved clockwise and/or counterclockwise in the torsional direction as shown by arrow R. When one or more length segments or portions of the handle shaft is/are moved in the torsional direction, such one or more length segments or portions is/are rotated about their longitudinal axes, respectively.

The entire or less than the entire length of the handle shaft 20 between member 18 and handle 22 can be moved or shaped longitudinally in the horizontal and/or vertical directions and/or torsionally in the torsional direction to achieve a desired overall shape or configuration for handle shaft 20. Where the entire length of the handle shaft does not have to be moved or shaped in order to obtain a desired overall configuration, one or more selected length segments or portions of the handle shaft can be moved or shaped longitudinally in the horizontal and/or vertical directions and/or torsionally in the torsional direction as needed to obtain the desired overall configuration. A single length segment or portion of the handle shaft can be moved or shaped in more than one direction. Different length segments or portions of the handle shaft can be moved or shaped in different directions from one another. The handle shaft can thusly be made to assume a virtually limitless variety of different configurations in response to manual shaping or adjustment by the surgeon or other operator.

Once the handle shaft has been shaped to assume a desired configuration, the handle shaft maintains the desired configuration without further intervention by the surgeon or other operator. Accordingly, the handle shaft is sufficiently rigid and strong to maintain its shape until it is deliberately reshaped. The manual force required to shape the handle shaft is preferably minimized to allow shaping by the surgeon or other operator without undue exertion. However, the strength and rigidity of the handle shaft is preferably great enough to prevent the handle shaft from losing its shape when subjected to the forces encountered during use.

By adjusting the configuration of the handle shaft, the handle shaft can be selectively shaped to reach an operative site in or on a patient from a location remote to the operative site. In particular, the handle shaft can be selectively shaped for accommodation or introduction in an anatomical path or passageway providing communication with an internal operative site from externally of the patient's body. For example, the handle shaft can be shaped to conform to the shape of the anatomical path or passageway and/or to avoid, circumvent or go around obstacles in the path or passageway, including anatomical obstacles such as anatomical tissue or structure and/or mechanical obstacles such as instruments or other equipment used during the procedure being performed. In this manner, the ultrasound emitting member 18 can be positioned at the internal operative site with the handle shaft 20 extending through the anatomical path or passageway so that the handle 22 is disposed externally of the patient's body.

Adjustment of the configuration of the handle shaft 20 is also used to selectively adjust the orientation of the ultrasound emitting member 18. For example, by bending, curving and/or twisting the handle shaft 20, the active face 32 can be selectively oriented vertically, horizontally, transversely and/or at various angles relative to the handle shaft and/or relative to the longitudinal axis of the handle including being oriented perpendicular to the longitudinal axis of the handle. In particular, the active face can be oriented to face upwardly, downwardly, forwardly and laterally from the handle shaft and/or the handle as well as at various angles thereto. In this manner, the orientation of the active face can be selectively adjusted without changing the orientation of the handle for grasping by the surgeon or other operator. In other words, the handle can be in the operative orientation or position when grasped by the surgeon or other operator while the active face may be disposed in various different orientations relative to the longitudinal axis of the handle. Thus, the handle can be optimally grasped in the same manner for different orientations of the active face. It is not necessary, therefore, to turn or rotate the handle for grasping or to otherwise have the handle in an awkward position during use.

In FIG. 1, the handle 22 is in the operative position, and the active face 32 is oriented horizontally relative to the handle shaft 20 and the handle. The active face 32 faces upwardly from the handle shaft 20 and defines a top or upper wall or surface for the ultrasound emitting member 18. As explained further below, the orientation of active face 34 relative to the handle as shown in FIG. 1 is advantageous for use in ablating the soft palate.

One or more electrical transmission wires 44 is/are connected to the transducer 24 and extend through the handle shaft 20 for connection with power supply 14 in order to transmit or supply electric current from the power supply to the transducer. The power supply may be disposed partly or entirely in the handle, or may be provided separately as a console or unit coupled to the handle shaft or the handle via one or more appropriate transmission wires, which may be the same or different from the one or more transmission wires 44. For example, an electrical cord of suitable length may be removably coupled between the handle 22 and the power supply 14. The power supply 14 can be designed in various ways as a source or supply of electricity to activate or excite transducer 24 to generate and emit ultrasound energy. For example, the power supply can be designed to provide high frequency alternating electrical current to the transducer via the one or more transmission wires. The power supply may include an RF generator, with or without an amplifier, providing a constant current source. Electrical current provided by the power supply is selectively discharged into all or selected ones of the piezoelectric elements producing vibration of all or selected ones of the piezoelectric elements and, therefore, producing acoustic or ultrasonic waves or energy. The power supply may be separate from the handle but may be operated via controls 42 on the handle.

In the case of focused ultrasound ablation device 12, a transmission wire 44 is provided for each piezoelectric element and, therefore, for each transducer element. As shown in FIG. 2, each transmission wire 44 is connected to its corresponding piezoelectric element and to the power supply so that the transducer elements are individually driven by or supplied with current from the power supply. The transmission wires 44 are disposed in respective passages within the housing and may be disposed within a sheath or sleeve 46 extending through shaft 20. The transmission wires 44 are connected to switches (not shown), respectively, for controlling the supply or transmission of current from the power supply 14 to the piezoelectric elements, respectively. The switches can be incorporated in the ultrasound emitting member 18, the power supply 14 and/or the controller 16.

The controller or control unit 16 controls the supply of power from power supply 14 to the transducer so that the transducer can be driven to deliver various intensity levels of ultrasound energy for various durations, periods or lengths of time. In particular, the controller 16 controls the supply of power from the power supply to the individual piezoelectric elements so that the transducer elements can be individually driven or actuated to emit ultrasound energy. The controller, which may be designed as part of the power supply, will typically include a control panel and display monitor, one or more switches for current control, an input mechanism such as a keyboard, and/or a microprocessor including memory, storage and data processing capabilities for performing various functions. The controller is capable of selectively activating the switches for the transducer elements to "fire" or effect actuation of all or selected ones of the plurality of transducer elements to emit ultrasound energy. For example, switches on the controller 16 and/or the controller keyboard can be used to selectively couple and decouple the individual transducer elements 28 with the electrical drive signal or current from the power supply 14.

Input to the controller 16 provided by the surgeon or other medical personnel determines the transducer elements 28 to be actuated. For example, data entered via the controller keyboard is used to identify the particular transducer elements to be actuated, the transducer elements being identified, for example, by their location or position in the array as explained above. In this manner, the switches of selected transducer elements can be activated to permit transmission of electrical current from the power supply to the piezoelectric elements of the selected transducer elements while the switches of other selected transducer elements can remain deactivated to prevent transmission of electrical current thereto when the power supply is actuated or switched to an "on" mode. It should be appreciated that various components and/or methodology can be incorporated in the device 12, including the power supply 14 and/or the controller 16, to permit selective actuation of selected ones of the transducer elements 28 and that such components and/or methodology would be within the purview of one skilled in the art.

An alternative focused ultrasound ablation device 112 for use in the methods of the present invention is illustrated in FIG. 4. The focused ultrasound ablation device 112 is similar to device 12 and includes ultrasound emitting member 118 carried by malleable handle shaft 120, which is longitudinally adjustable in the vertical direction as shown by arrow Y and in the horizontal direction and is torsionally adjustable as shown by arrow R. The ultrasound emitting member 118 for device 112 includes a single transducer element 128 disposed within housing 126 and being capable of generating and emitting ultrasound energy in response to being supplied with electrical power from the power supply. The transducer element 128 includes a piezoelectric element that vibrates to produce ultrasound energy when electrical current is supplied thereto. The piezoelectric element is electrically coupled to the power supply during use, such as via a transmission wire (not shown) and has a concave configuration causing the ultrasound energy generated thereby to be focused, as shown by arrows in FIG. 4, at a focusing zone F located fixed distance. D from an active face 132 of housing 126.

The housing 126 has a generally rectangular configuration with a wall 132 thereof defining the active face for member 118. The transducer element 128 is disposed in housing 126; however, the transducer element can be carried externally on the housing and/or can partly or entirely form or define the active face of the housing. The piezoelectric element for transducer element 128 is movably supported on a platform 148 in housing 126. The platform 148 is parallel to active face 132, and both the platform and active face are planar. The piezoelectric element is curved in a direction away from active face 132 such that ultrasound energy generated thereby passes through active face 132 for focusing at the focusing zone F, the active face or housing wall being made of a material through which ultrasound energy can pass. Accordingly, when the wall of housing 126 is positioned externally adjacent or in contact with a mass, body or area of anatomical tissue A, the ultrasound energy emitted by transducer element 28 is focused at zone F, which will be disposed within the anatomical tissue A as shown in FIG. 4.

The piezoelectric element is supported on a base member 150 which rides along tracks in or on platform 148. The base member can include a motor, or a motor can be mounted elsewhere in the housing 126, for moving the base member and, therefore, the piezoelectric element, along the tracks. The tracks, which can be formed by grooves in the platform receiving a tongue of the base member, extend lengthwise and widthwise in a grid pattern along the platform. The platform has a length and width the same as or substantially the same as the length and width of the housing. Accordingly, the piezoelectric element is movable longitudinally, i.e. lengthwise, in forward and rearward directions in the housing as shown by an arrow in FIG. 4. Also, the piezoelectric element is movable transversely, i.e. side to side, in the housing in a direction perpendicular to the arrow.

By selecting and controlling the range of movement of the transducer element 128, via the controller, in the longitudinal and transverse directions, a scanning effect is obtained by which the focusing zone F is moved within the tissue while the member 118 remains stationary and does not move relative to the tissue. For example, the transducer element 128 is illustrated in dotted lines in FIG. 4 moved longitudinally, forwardly to produce a focusing zone F' forwardly of focusing zone F. By "firing" the transducer element to emit ultrasound energy as it is moved longitudinally and/or transversely, a designated target area in the tissue can be linearly scanned with focused ultrasound energy so that the tissue is heated to an ablative temperature at various focusing zones throughout the target area to form a lesion, such as lesion 138. Also, by selecting and controlling the range of movement of the piezoelectric element in the longitudinal and transverse directions via the controller, which directs the motor to move the transducer element the selected range, a lesion of desired size and configuration is obtained. Accordingly, transducer element 128 can be used to form lesions of various sizes and shapes. The housing wall 132 may be rigid or flexible or deformable depending on procedural use and may be formed as a flexible membrane. Where the housing wall 132 is flexible or deformable, the active face is capable of conforming to the shape of the tissue surface against which it is placed. Of course, where soft tissue is being ablated, the soft tissue will confirm to the shape of the active face where the active face is more rigid than the soft tissue.

The ultrasound emitting member 118 can include a temperature sensor 141, such as a thermocouple, for sensing the temperature at the transducer/tissue interface. The temperature sensor can be disposed on or in the housing, can be disposed externally of the housing or can be disposed on, in or externally of the transducer. Depending on the design of the temperature sensor, the temperature sensor may penetrate the tissue slightly. The temperature sensor 141 is embedded in the housing wall 132. During use, the temperature sensor 141 detects the temperature of the tissue at the transducer/tissue interface, i.e. the junction of the active face with the external tissue surface. The controller can be programmed to effect automatic shut down of the ablation device 112 when the temperature sensed by the temperature sensor reaches or exceeds a predetermined temperature. The predetermined temperature can be selected by the surgeon or other operator and provided as input to the controller. By automatically terminating ultrasound energy delivery to the tissue when a preselected temperature at the transducer/tissue interface is reached or exceeded undesired tissue damage and fistula formation are avoided.

It should be appreciated that the focused ultrasound ablation devices can be provided with imaging capabilities for visualizing operative sites at which the focused ultrasound ablation devices are to be used, for visualizing guidance and/or positioning of the ultrasound emitting members at the operative sites and/or for examination and diagnosis as disclosed in the patent applications incorporated herein by reference.

FIG. 5 illustrates another alternative focused ultrasound ablation device 212 having a transducer element 228 operated in a manner similar to transducer element 128 so that the transducer element 228 is movable longitudinally as shown in dotted lines and by the arrow in FIG. 5 as well as transversely as described for transducer element 128. The transducer element 228 is formed by a flat or planar piezoelectric element and a concave lens 252 that focuses ultrasound energy produced by the piezoelectric element at a focusing zone located a predetermined perpendicular distance from the active face 232. The piezoelectric element is electrically coupled to the power supply during use, such as via a transmission wire (not shown). The lens 252 is made of ultrasound transmitting material and has a specific focusing configuration or geometry to obtain focusing of the ultrasound energy at a focusing zone located a predetermined distance from the active face. A space or cavity 254 is defined in the housing 226 around the transducer element 228. The handle shaft 220 has inlet and outlet conduits 256 and 258, respectively, extending therethrough. The inlet conduit 256 communicates or is coupled with a source or supply of cooling medium, such as cooling fluid, adapted to be introduced or pumped therethrough. The inlet and outlet conduits 256 and 258 communicate with the space 254 such that the cooling medium carried by the inlet conduit enters the space and is positively or actively withdrawn from or is passively forced from the space through the outlet conduit. In this manner, a cooling medium such as water can be introduced into and withdrawn from the housing 226, which can be fluidically sealed, in order to dissipate heat in the housing and effect cooling of the ultrasound emitting member 218 including cooling of the active face. In this manner, cooling of the external tissue surface and, in particular, the mucosal surface, is effected to further avoid unwanted tissue damage and reduce the risk of fistula formation. The handle shaft 220 is malleable to permit torsional adjustment thereof, as represented by arrow R, and longitudinal adjustment thereof in the vertical direction, as represented by arrow Y, and in the horizontal direction.

A further alternative focused ultrasound ablation device for use in the methods of the present invention is illustrated in FIG. 6 at 312 and includes an ultrasound emitting member 318 that is representative of an ultrasound emitting member wherein the transducer is acoustically coupled to the tissue via a coupling medium. The ultrasound emitting member 318 is also representative of an ultrasound emitting member that is mechanically moved to linearly scan a target area with high intensity focused ultrasound. The ultrasound emitting member 318 is disposed at the distal end of an inner handle shaft 320a, which is movably disposed in an outer handle shaft 320b. The member 318 includes transducer element 328 formed by a curved piezoelectric element disposed in housing 326, the wall 332 of which is formed by a resilient, flexible or elastic membrane 335. A transmission wire 344 extends through inner shaft 320a and is connected to the piezoelectric element for electrically coupling the piezoelectric element with the power supply. An acoustic coupling medium such as an acoustic fluid or gel 337 capable of transmitting ultrasound occupies the space between the membrane and the piezoelectric element. The coupling medium can be introduced in and removed from the housing, which can be fluidically sealed, via a conduit 349 extending through inner shaft 320a and communicating with the space between the membrane and the piezoelectric element.

Ultrasound energy produced by the piezoelectric element in response to electrical excitation thereof propagates or passes through the coupling medium, which acoustically couples the transducer element to anatomical tissue positioned in contact with the membrane. The membrane has a somewhat bulging shape due to the presence of the coupling medium; however, the membrane is capable of flattening or conforming to the shape of the tissue surface against which it is placed. The ultrasound emitting member 318 is therefore representative of an ultrasound emitting member having a flexible or deformable active face. The ultrasound emitting member 318 is representative of an ultrasound emitting member wherein the coupling medium is formed as part of the ultrasound emitting member. It should be appreciated, however, that the coupling medium can be provided in a device separate from the ultrasound emitting member and interposed between the anatomical tissue and the ultrasound emitting member.

The inner shaft 320a is reciprocatively movable longitudinally, forwardly and rearwardly, relative to and within the outer shaft 320b to control the extension of member 318 distally from beyond the outer shaft. Accordingly, the member 318 can be retracted and extended relative to the outer shaft to protrude or extend a desired extension distance beyond the outer shaft, the member 318 being illustrated in FIG. 6 fully exposed from the outer shaft. The handle for focused ultrasound ablation device 312 can be provided with a motor or other mechanism for moving the inner shaft longitudinally relative to the outer shaft. Longitudinal extension of the member 318 can begin with the member 318 fully exposed from the outer shaft or disposed partly or entirely within the outer shaft, the member 318 being accommodated in the outer shaft due to flattening of the active face. As the member 318 is extended relative to the outer shaft while the transducer element 328 is "fired" to emit ultrasound energy, tissue adjacent the membrane is scanned with high intensity focused ultrasound, and a similar effect is achieved when the member 318 is retracted from an extended position. In this manner, the focusing zone for the piezoelectric element is moved linearly within the tissue to cause heating of a designated target area and formation of a subsurface lesion of desired size and shape, the size and shape being dictated by the range of movement or reciprocative stroke for member 318. The device 312 can be programmed via the controller to obtain a desired lesion by selecting the appropriate extension distance and/or reciprocative stroke for the ultrasound emitting member.

The outer handle shaft 320b is malleable to permit longitudinal adjustment in the vertical direction, as shown by arrow Y, and in the horizontal direction. The outer handle shaft 320b is also torsionally adjustable as shown by arrow R. The inner handle shaft 320a is flexible to follow or conform to the shape or configuration of the outer handle shaft, and the inner handle shaft moves with the outer handle shaft as the outer handle shaft is adjusted longitudinally and/or torsionally. The handle shaft can be designed in various ways to achieve movement or adjustment of the inner handle shaft with the outer handle shaft while allowing the inner handle shaft to move longitudinally relative to and within the outer handle shaft. As an example, the inner handle shaft 320a has an external protrusion 321 received in a longitudinal channel formed internally in the outer handle shaft 320b. Engagement of the protrusion with the channel causes the inner handle shaft to be moved or adjusted with the outer handle shaft. The protrusion is movable forwardly and rearwardly within the channel allowing the inner handle shaft to move longitudinally, forwardly and rearwardly, within the outer handle shaft.

Various transducers can be used in the focused ultrasound ablation devices of the present invention. An individual transducer can include a single piezoelectric or other transducer element, an annular array of such elements, a linear array of such elements, and/or a curved linear array of such elements. More than one transducer can be provided in a single ultrasound emitting member. The piezoelectric elements can be made of various piezoelectric materials such as PZT crystal materials, hard lead, zirconate/lead titanium piezoelectric ceramic, or lithium-niobate piezoceramic material. The transducer elements can be of various sizes and can have various focusing geometries. Exemplary transducers that may be used or modified for use in the devices of the present invention are disclosed in U.S. Pat. Nos. 4,858,613, 4,955,365 and 5,036,855 to Fry et al, U.S. Pat. No. 5,117,832 to Sanghvi et al, U.S. Pat. Nos. 5,492,126 and 5,520,188 to Hennige et al, U.S. Pat. No. 5,676,692 to Sanghvi et al and U.S. Pat. No. 5,762,066 to Law et al, the disclosures of which are incorporated herein by reference. The frequency ranges of the transducers can vary depending on clinical needs. Transducer frequencies may be in the range of 0.5 to 12 MHz and, more typically, in the range of 5 to 12 MHz. Preferably, the transducer frequency will allow thermal ablation of anatomical tissue to be effected in response to the application or delivery of ultrasound energy to the tissue for a relatively short duration or length of time. In accordance with the present invention, the duration or length of time for ultrasound energy delivery or application to the tissue preferably ranges from 2–45 seconds depending on desired lesion size and/or ablative effect.

The focused ultrasound ablation devices of the present invention, are used to ablate target areas within tissue to create ablative lesions. Depending on the characteristics of the lesions, such as the dimensions of the lesions, the severity of tissue damage and/or the nature of the ablated tissue, all or part of the lesions may be naturally degraded and absorbed by the patient's body or may remain as altered tissue, such as scar tissue that is more stiff or firm than the untreated tissue. Accordingly, the lesions may be entirely absorbed, may remain entirely as scar or other altered tissue, or may be partly absorbed and partly remaining as scar or other altered tissue. Where the lesions are partly or entirely absorbed, the tissue may shrink or decrease in size. In this manner, the size or volume of the tissue may be reduced and/or the configuration of the tissue may be changed in order to treat various disorders or conditions, such as by increasing the sizes of anatomical passageways, cavities or other spaces. Where the lesions remain partly or entirely as altered tissue, the altered tissue may be stiffer, firmer or more rigid than normal undamaged tissue. In addition, the altered tissue may contract, thusly reducing the size of the tissue and correspondingly increasing the sizes of anatomical passageways, cavities or other spaces. It should be appreciated that regardless of whether the lesions are absorbed and eliminated or remain as altered tissue, partly or entirely, the tissue is nonetheless "reduced". Accordingly, as used herein, "reduction" of the anatomical tissue involves elimination or reduction of normal tissue by absorption of ablated tissue and/or by transformation of normal undamaged tissue into altered tissue.

FIG. 7 illustrates use of focused ultrasound ablation device 12 to ablate the soft palate of a patient to treat various airway associated disorders in a manner similar to that disclosed in the application incorporated herein by reference and entitled Methods of Soft Palate Reduction By Thermal Ablation Using High Intensity Focused Ultrasound.

As shown in FIG. 7, the handle shaft 20 has been shaped by the surgeon or other operator so that the active face 32 faces upwardly from the handle shaft and relative to the handle. The active face 32 is placed against the soft palate S with the handle shaft extending through the patient's mouth M and the handle disposed externally of the patient's body. In particular, the handle shaft 20 has been shaped longitudinally to assume a longitudinally shaped position with a distal length segment or portion of handle shaft 20 bent, curved or moved downwardly in the vertical direction to follow or conform to the curvature of the oral cavity, as defined between the tongue and the roof of the mouth, from the soft palate S to the opening of mouth M. The handle shaft 20 is thusly accommodated in the anatomical passageway presented by mouth M and follows the longitudinal configuration thereof to position the active face 32 in contact with soft palate S at a selected operative site. The curvature imparted to the handle shaft is such that the active face is disposed at the necessary angle to contact the soft palate at the selected operative site without the handle shaft exerting damaging pressure or force on the anatomical tissue or structure of the oral cavity so that surrounding anatomical tissue and structure are not traumatized. The handle is in the operative position or orientation when grasped and held by the surgeon and is used to guide the handle shaft through the anatomical passageway as well as to hold the active face against the soft palate S.

The active face is placed at or on the soft palate at a location aligned with a desired target area in the soft palate. Also, all or specific ones of the transducer elements are selected for actuation or "firing" in accordance with the size and configuration of a lesion desired to be formed at the target area. The device 12 is programmed via the controller to effect actuation or "firing" of the selected transducer elements when electric current or a signal is supplied to the transducer. Of course, selection and programming for actuation or "firing" of selected transducers can be performed prior to introduction or positioning of member 18 at the operative site. In the procedure illustrated in FIG. 7, the active face 32 is positioned in contact with the external tissue surface or mucosa 36 of the soft palate S at a location anteriorly of and slightly to one side of the uvula U.

Once the active face is positioned in contact with the soft palate S at the desired location, the power supply is activated or switched to an "on" mode to transmit electrical energy to the previously selected transducer elements. In response thereto, the piezoelectric elements vibrate and produce ultrasound energy, which is focused within the soft palate S at the corresponding focusing zones. Accordingly, anatomical tissue at the target area is heated to an ablative temperature causing an ablative lesion 238 to be formed in the soft palate S, as shown in FIG. 7, while the ultrasound emitting member 18 remains external of and does not physically penetrate the soft palate S. In addition, tissue surrounding the target area is not heated to damaging levels. The lesion 238 has a length, width and depth of known parameters depending on the locations of the selected transducer elements, the intensity of the ultrasound energy, the length of the focusing zones, the temperature to which the tissue is heated, and the duration of ultrasound energy delivery or application to the tissue. The lesion can have various surface configurations including rectangular, square and circular configurations.

Due to the predetermined distance D and the known length of the focusing zones, the lesion 238 begins at a beginning or starting margin 264 located a predetermined or known depth beneath or below the external tissue surface 36 and ends at an ending margin 266 located a predetermined or known depth beneath the external tissue surface 36, the distance between the beginning and ending margins corresponding to the depth of the lesion. By selecting the appropriate focusing zone depth in the tissue, a desired thickness or depth of tissue between the beginning margin 264 and the external tissue surface 36 is disposed outside the target area and is therefore undamaged and preserved. By selecting the appropriate focusing zone length, the depth of the ending margin within the tissue is controlled thusly ensuring that the lesion does not extend deeper than desired. In the illustrated procedure, the starting margin is disposed a desired depth or distance beneath or below the external surface 36. However, it should be appreciated that the starting margin can be at or coincident with the external surface 36 depending on the particular procedure. Although the length and width or other external dimensions of the lesion can be determined by the locations of the "fired" transducer elements, it should be appreciated that the length and/or width of the lesion can alternatively be obtained by manually moving the member 18 from site to site on the tissue as described in the co-depnding patent applications incorporated herein by reference.

The emission of ultrasound energy by ultrasound emitting member 18 is terminated by the surgeon or other operator once a desired lesion size or amount of tissue ablation has been obtained, and the member 18 is withdrawn from the oral cavity or other operative site. In order to terminate the emission of ultrasound energy by the ultrasound emitting member, the power supply is deactivated or switched to an "off" mode, so that electrical current is no longer supplied to the selected piezoelectric elements. Where one or more additional lesions are to be formed in the oral cavity, the member 18 can be repositioned in the oral cavity such that the active face contacts tissue at another selected operative site. Where readjustment of the handle shaft is not needed, the member 18 can be repositioned in the oral cavity without withdrawal of the handle shaft therefrom. However, where readjustment of the handle shaft is needed to facilitate or allow positioning of the active face at the another selected operative site, the handle shaft is withdrawn from the oral cavity and readjusted or reshaped as necessary prior to positioning the ultrasound emitting member at the another selected operative site.

FIG. 8 illustrates the handle shaft 20 shaped longitudinally and torsionally so that the ultrasound emitting member 18 has its active face facing anteriorly, distally or forwardly from the handle shaft 20 and relative to the handle. In particular, a sharp lateral bend has been imparted to a distal length portion of the handle shaft in the horizontal direction. Also, the distal length portion has been twisted torsionally about its axis so that the active face is at the front of the ultrasound ablation device. In addition, the handle shaft has been bent or curved in the vertical direction to be longitudinally shaped for accommodation in the oral cavity as described for the procedure of FIG. 7. The handle shaft has thusly been shaped to assume longitudinally and torsionally shaped positions by which the ultrasound emitting member has its longitudinal axis or length extending transverse to a proximal length portion of the handle shaft. When the active face is placed against the soft palate S as shown in FIG. 8, the longitudinal axis of member 18 extends transverse or perpendicular to uvula U, and the longitudinal configuration of the handle shaft conforms or substantially conforms to the longitudinal configuration of the anatomical passageway. FIG. 9 illustrates in dotted lines a rectangular subsurface lesion 338 formed in the soft palate S with the ultrasound emitting member 18 positioned as shown in FIG. 8. The lesion 338 is centrally located on the soft palate S anteriorly of and in alignment with uvula U, with the length of the lesion 338 extending transverse or perpendicular to the uvula U.

Figure 10:
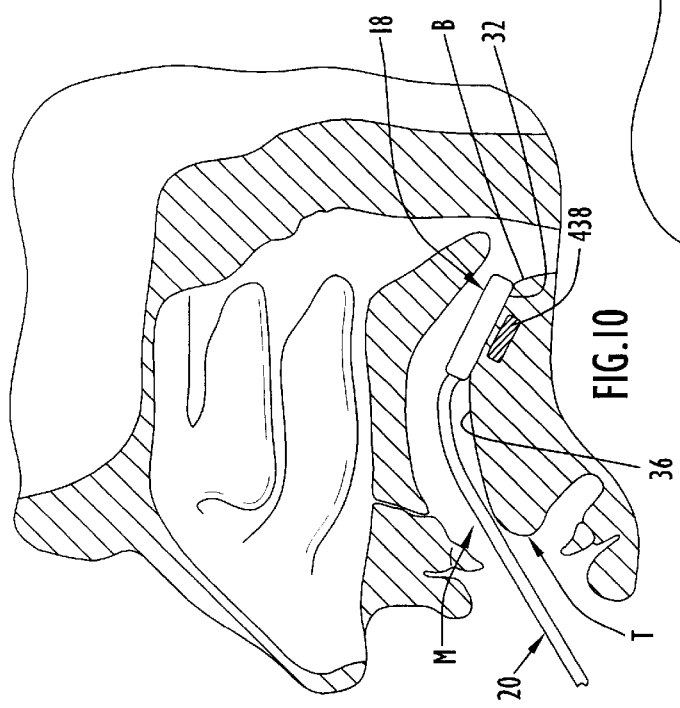
FIG. 10 is a broken side view, partly in section, illustrating the handle shaft of the focused ultrasound ablation device of FIG. 1 adjusted to position the active face of the ultrasound emitting member against the base of the tongue of a patient to create an internal lesion.

FIG. 10 illustrates use of the focused ultrasound ablation device 12 to ablate the tongue of a patient in a manner similar to that disclosed in the patent application entitled Methods of Tongue Reduction By Thermal Ablation Using High Intensity Focused Ultrasound and incorporated herein by reference. FIG. 10 illustrates the handle shaft 20 shaped by the surgeon or other operator longitudinally and torsionally so that the active face 32 faces and is placed against the base B of tongue T with the handle shaft 20 extending through the patient's mouth M with the handle disposed in the operative position externally of the patient's body. In particular, the handle shaft 20 has been manually twisted or rotated in the torsional direction, about its own longitudinal axis, such that the active face 32 faces downwardly from the handle shaft and relative to the handle with the handle in the operative position. In this torsionally shaped position, the active face is disposed on a side of handle shaft 20 opposite controls 42. In addition, a distal length portion of handle shaft 20 has been bent or curved downwardly in the vertical direction; and, in this longitudinally adjusted position, the handle shaft follows or conforms to the curvature of the oral cavity from the base B of tongue T to the opening of mouth M. The longitudinal configuration of the handle shaft thusly conforms or substantially conforms to the longitudinal configuration of the anatomical passageway presented by mouth M and is accommodated in the anatomical passageway presented by mouth M to position the active face in contact with the base B of tongue T. The longitudinal curvature imparted to the handle shaft is such that the active face is disposed at the necessary angle to contact the base B of tongue T without the handle shaft exerting traumatizing pressure or force on surrounding anatomical tissue or structure. The handle is in the operative position or orientation when grasped and held by the surgeon or other operator and is used to guide the handle shaft through the anatomical passageway as well as to hold the active face against the tongue T.

In the procedure illustrated in FIG. 10, the active face 32 is positioned in contact with the external tissue surface or mucosa 36 of the tongue T, at a location aligned with a selected target area in the tongue. The power supply is activated or switched to an "on" mode to transmit electrical energy to selected transducer elements. In response thereto, the selected transducer elements vibrate and produce ultrasound energy, which is focused at one or more focusing zones contained in the target area Anatomical tissue at the target area is heated to an ablative temperature to form lesion 438 while tissue surrounding the target area is not heated to damaging levels. The lesion 438 has a length, width and depth of known parameters corresponding to the locations of the selected transducer elements, the intensity of the ultrasound energy, the length of the focusing zones and the duration of energy delivery or application to the tissue.

Figure 12:
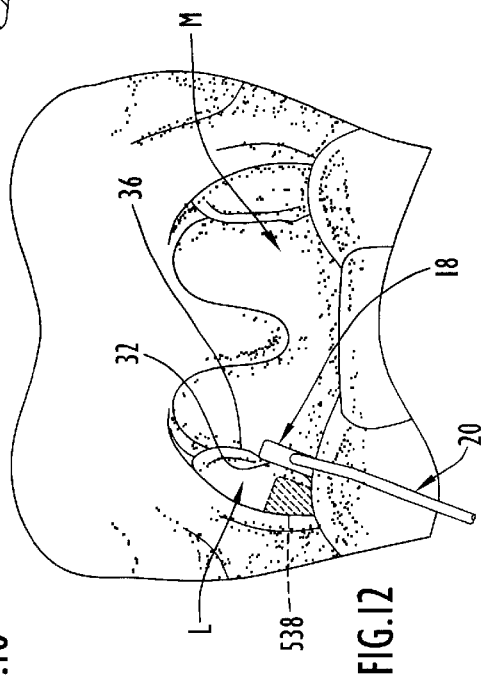
FIG. 12 is a broken anterior view of the patient's oral cavity illustrating the active face placed against the tonsil and the internal lesion formed therein.

FIGS. 11 and 12 illustrate use of focused ultrasound ablation device 12 to ablate a tonsil of a patient in a manner similar to that disclosed in the application incorporated herein by reference and entitled Methods of Tonsil Reduction By Thermal Ablation Using High Intensity Focused Ultrasound. FIGS. 11 and 12 illustrate the handle shaft 20 shaped by the surgeon or other operator longitudinally and torsionally so that the active face 32 faces laterally or sideways from the handle shaft and relative to the handle. The active face is placed against a tonsil L with the handle shaft 20 extending through the patient's mouth M with the handle in the operative position grasped externally of the patient's body. In FIGS. 11 and 12, the handle shaft 20 has been twisted or rotated in the torsional direction, about its own longitudinal axis, to assume a torsionally shaped position in which the active face 32 faces laterally or sideways from the handle shaft with the handle in the operative position. A distal length portion of handle shaft 20 has also been curved or bent downwardly in the vertical direction; and, in this longitudinally shaped position, the longitudinal configuration of handle shaft 20 follows or conforms to the longitudinal configuration of the oral cavity M from the tonsil L to the opening of the oral cavity M. The handle shaft 20 is thusly accommodated in the anatomical passageway presented by oral cavity M to position the active face 32 in contact with the tonsil L at a selected operative site aligned with a target area in the tonsil at which a lesion is desired to be formed. In the illustrated procedure, the active face 32 is placed in contact with an outer side of tonsil L. The active face is thusly disposed in the orientation needed for the active face to contact the tonsil L at the selected operative site while the handle shaft extends through the oral cavity M without any damaging force or pressure exerted on surrounding anatomical tissue or structure. The handle is in the operative position or orientation when grasped and held by the surgeon or other operator and is used to guide the handle shaft through the anatomical passageway as well as to hold the active face against the tonsil L.

As shown in FIG. 12, the active face 32 is positioned in contact with the external tissue surface 36 at a location at or near the bottom or lower end of the outer side of right tonsil L. Once the active face is positioned in contact with the tissue of the tonsil T at the desired location, the power supply is activated to transmit electrical energy to previously selected transducer elements. In response thereto, the piezoelectric elements of the previously selected transducer elements vibrate and produce ultrasound energy, which is focused at corresponding focusing zones within the target area. The target area is heated to an ablative temperature with the focused ultrasound energy causing a lesion 538 to be formed in the right tonsil L, as shown in FIGS. 11 and 12, while the ultrasound emitting member 18 remains external of and does not physically penetrate the right tonsil L. Moreover, the tissue surrounding the target area is not heated to damaging levels.

Figure 14:
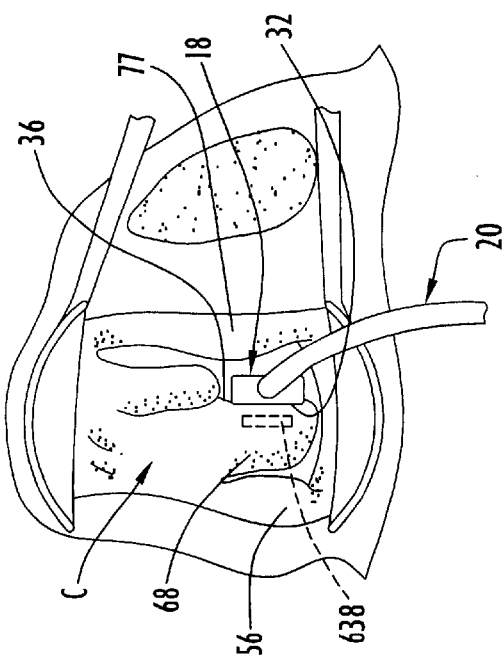
FIG. 14 is a broken bottom view of the patient's nasal cavity illustrating the active face placed against the turbinate and the internal lesion formed therein.
Figure 13:
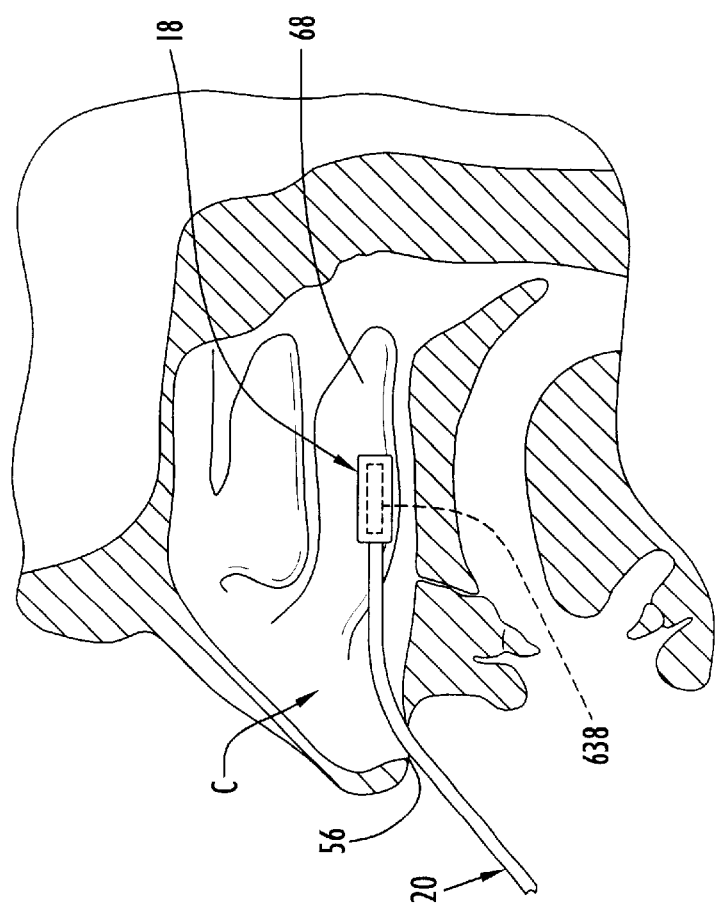
FIG. 13 is a broken side view, partly in section, illustrating the handle shaft of the focused ultrasound ablation device of FIG. 1 adjusted to position the active face against a turbinate of a patient to create an internal lesion.

FIGS. 13 and 14 illustrate use of the focused ultrasound ablation device 12 to ablate a turbinate of a patient in a manner similar to that disclosed in the patent application incorporated herein by reference and entitled Methods of Turbinate Soft Tissue Reduction By Thermal Ablation Using High Intensity Focused Ultrasound.

FIGS. 13 and 14 illustrate the handle shaft 20 shaped by the surgeon or other operator longitudinally and torsionally so that the active face 32 faces laterally or sideways from the handle shaft 20 and relative to the handle. The active face is placed against an inferior turbinate 68 with the handle shaft extending through the patient's nostril 56 with the handle in the operative position grasped externally of the patient's body. The handle shaft 20 has been twisted or rotated in the torsional direction to assume a torsionally shaped position, similar to the torsionally shaped position assumed by the handle shaft in FIGS. 11 and 12, such that the active face 32 faces laterally or sideways from the handle shaft with the handle in the operative position. A distal length portion of handle shaft is curved or bent in the vertical direction to assume a longitudinally shaped position following or conforming to the configuration of the right nasal cavity C from the inferior turbinate 68 to external of the patient's body. The active face is thusly disposed in the orientation needed to contact the inferior turbinate 68 at the selected operative site, which is aligned with a target area in or on the inferior turbinate, while the handle shaft extends through the nasal cavity without traumatizing force or pressure exerted on surrounding anatomical tissue or structure. The handle is in the operative position or orientation when grasped and held by the surgeon or other operator and is used to guide the handle shaft through the nasal cavity as well as to hold the active face against the inferior turbinate.

The ultrasound emitting member 18 is disposed between the inferior turbinate 68 and the medial nasal wall 77, as shown in FIG. 14, with the active face 32 positioned in contact with the external tissue surface 36 of inferior turbinate 68 at a location between the interior and posterior ends. Once the active face is positioned in contact with the tissue of the turbinate 68 at the desired location, the power supply is activated to transmit electrical energy to previously selected transducer elements causing ultrasound energy to be emitted and focused at focusing zones within the target area. Accordingly, tissue at the target area is heated to an ablative temperature causing a lesion 638 to be formed in the turbinate 68 while the ultrasound emitting member remains external of and does not physically penetrate the turbinate. Additionally, the tissue surrounding the target area is not heated to damaging levels.

With the present invention, a single focused ultrasound ablation device can be used at various different operative sites at different anatomical locations since the handle shaft can be shaped, as needed, to access the operative sites from a location or locations remote from the operative sites. Where the operative sites are within patients' bodies, the handle shaft can be shaped for accommodation in anatomical passageways or cavities providing access to the internal operative sites from externally of the patients' bodies. The handle shaft can be shaped to circumvent or avoid anatomical tissue or structures in the anatomical passageways or cavities to avoid tissue damage and trauma.

The handle shafts can be shaped as needed to orient the ultrasound emitting members for contact with various tissue structures at various different operative sites. In particular, the active faces of the ultrasound emitting members can be oriented at various angles relative to the handle shafts and/or the handles, and/or to face in various directions from the ablation devices. For example, the active faces can be oriented vertically, horizontally, transversely, forwardly or at various angles therebetween. The active faces can be oriented to face upwardly, downwardly, laterally or forwardly from the ablation devices or at various positions therebetween. By shaping the handle shafts, the ultrasound emitting members can thusly be selectively positioned so that ultrasound energy is emitted from the ultrasound emitting members in desired directions in accordance with the locations of the target areas for ablative lesions in tissue.

The handle can be disposed in the same or substantially the same orientation each time it is grasped by a surgeon or other operator while the handle shaft can be disposed in various different shaped or adjusted configurations. Consistency of operation and feel is thusly maintained regardless of the configuration of the handle shaft. Where the handle is provided with hand-operated controls, the controls can be optimally oriented or positioned relative to the hand grasping the handle for various different configurations of the handle shaft.

The ultrasound ablation devices of the present invention can be used in various areas in or on the bodies of patients including areas of the head and neck. Adjustability provided by the malleable handle shafts expands the areas of use for the focused ultrasound ablation devices. Exemplary areas of use include, but are not limited to, the soft palate, tongue, tonsils, turbinates or other soft tissue of the head or neck and the skin.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A focused ultrasound ablation device for creating a lesion at a target area in anatomical tissue of a patient comprising an ultrasound emitting member from which ultrasound energy is emitted and by which the emitted ultrasound energy is focused a predetermined distance from said ultrasound emitting member;

a handle shaft having a distal end at which said ultrasound emitting member is disposed and having a proximal end; and a handle at said proximal end of said handle shaft, said handle having an operative position in which said handle is disposed in a predetermined orientation for optimal grasping by a hand of an operator, said handle shaft being sufficiently malleable to assume a selected configuration in order to selectively position said ultrasound emitting member horizontally, vertically and transversely in a selected orientation at an operative site of a patient's body so that the ultrasound energy emitted by said ultrasound emitting member is focused at a selected target area in anatomical tissue of the patient to create a lesion at the target area while said handle remains in said predetermined orientation in said operative position.

2. The focused ultrasound ablation device as recited in claim 1 wherein said ultrasound emitting member focuses the ultrasound energy in front of said ultrasound emitting member.

3. The focused ultrasound ablation device as recited in claim 2 wherein said ultrasound emitting member includes an active face and the ultrasound energy is focused said predetermined distance from said active face.

4. The focused ultrasound ablation device as recited in claim 3 wherein said handle shaft, once shaped to assume a selected configuration, maintains said selected configuration until said handle shaft is shaped to assume another, different, selected configuration.

5. The focused ultrasound ablation device as recited in claim 4 wherein said handle shaft has a central longitudinal axis and is selectively, manually, torsionally adjustable by being rotated about said central longitudinal axis as permitted by the malleability of said handle shaft.

6. The focused ultrasound ablation device as recited in claim 4 wherein said handle shaft is selectively, manually, longitudinally adjustable to orient said active face to face a desired direction from said focused ultrasound ablation device.

7. The focused ultrasound ablation device as recited in claim 4 wherein said handle shaft is selectively, manually, longitudinally adjustable to orient said active face at various angles.

8. A focused ultrasound ablation device for creating a lesion at a target area in anatomical tissue of a patient comprising
    an ultrasound emitting member from which ultrasound energy is emitted and by which the emitted ultrasound energy is focused a predetermined distance from said ultrasound emitting member; and
    a handle shaft having a distal end at which said ultrasound emitting member is disposed and having a proximal end connected to a handle, said handle shaft having a length extending from said handle to said ultrasound emitting member, said handle shaft being malleable over the entirety of said length for selective, manual, adjustment in vertical and horizontal directions whereby said handle shaft is shapeable to assume a selected configuration in order to position said ultrasound emitting member at an operative site of a patient's body so that the ultrasound energy emitted by said ultrasound emitting member is focused at a selected target area in anatomical tissue of the patient to create a lesion at the target area while said handle is disposed at a location remote from the operative site.

9. A focused ultrasound ablation device for creating a lesion at a target area in anatomical tissue of a patient comprising
    an ultrasound emitting member from which ultrasound energy is emitted and by which the emitted ultrasound energy is focused at one or more focusing zones disposed a predetermined distance from a planar active face of said ultrasound emitting member;
    an elongate handle shaft having a central longitudinal axis, a distal end at which said ultrasound emitting member is disposed and having a proximal end; and
    a handle at said proximal end of said handle shaft, said handle shaft being malleable for selective, manual adjustment whereby said active face of said ultrasound emitting member is oriented to contact anatomical tissue of a patient so that the ultrasound energy emitted by the ultrasound emitting member is focused within a selected target area in the anatomical tissue to create a lesion at the target area while said handle is disposed in an operative position, said handle shaft being sufficiently malleable to orient said planar active face horizontally, vertically and transversely to said central longitudinal axis.

10. The focused ultrasound ablation device as recited in claim 9 wherein said handle shaft is adjustable, as permitted by its malleability, to orient said active face to be disposed at a selected angle to said handle.

11. The focused ultrasound ablation device as recited in claim 10 wherein said handle shaft is adjustable to orient said active face to face upwardly when said handle is in said operative position.

12. The focused ultrasound ablation device as recited in claim 11 wherein said handle shaft is adjustable to orient said active face to face downwardly when said handle is in said operative position.

13. The focused ultrasound ablation device as recited in claim 12 wherein said handle shaft is adjustable to orient said active face to face laterally when said handle is in said operative position.

14. The focused ultrasound ablation device as recited in claim 13 wherein said handle shaft is adjustable to orient said active face to face forwardly when said handle is in said operative position.

15. A focused ultrasound ablation device for creating a lesion at a target area in anatomical tissue of a patient comprising
    an ultrasound emitting member from which ultrasound energy is emitted and by which the emitted ultrasound energy is focused a predetermined distance in front of said ultrasound emitting member;
    an elongate handle shaft having a distal end at which said ultrasound emitting member is disposed and having a proximal end; and
    a handle at said proximal end of said handle shaft, said handle shaft being malleable for selective, manual adjustment in axial and torsional directions to selectively orient said ultrasound emitting member so that the ultrasound energy is emitted in a desired direction from said handle shaft whereby the ultrasound energy is focused at a selected target area in anatomical tissue adjacent said ultrasound emitting member while said handle is disposed at a location remote from the anatomical tissue.

16. The focused ultrasound ablation device as recited in claim 15 wherein said handle shaft is adjustable, as permitted by its malleability, to selectively orient said ultrasound emitting member so that the ultrasound energy is emitted in a direction laterally from said handle shaft.

17. The focused ultrasound ablation device as recited in claim 16 wherein said handle shaft is adjustable, as permitted by its malleability, to selectively orient said ultrasound emitting member so that the ultrasound energy is emitted in a direction laterally upwardly from said handle shaft.

18. The focused ultrasound ablation device as recited in claim 16 wherein said handle shaft is adjustable, as permitted by its malleability, so that the ultrasound energy is emitted in a direction laterally from a side of said handle shaft.

19. The focused ultrasound ablation device as recited in claim 16 wherein said handle shaft is adjustable, as permitted by its malleability, so that the ultrasound energy is emitted in a direction laterally downwardly from said handle shaft.

20. The focused ultrasound ablation device as recited in claim 18 wherein said handle shaft is adjustable, as permitted by its malleability, so that the ultrasound energy is emitted in a direction forwardly of said focused ultrasound ablation device.

21. A method of thermally ablating anatomical tissue of a patient comprising the steps of provinding a focused ultrasound ablation device comprising an ultrasound emitting member including an active face carried at a distal end of a malleable handle shaft having a proximal end connected to a handle having an operative position in which the handle is in a predetermined orientation for optimal grasping with a hand;

selecting one of a plurality of different orientations for the active face, said step of selecting including selecting an orientation in which the active face is oriented to contact anatomical tissue at an operative site of the patient's body while the handle is disposed at a location remote from the operative site;

manually shaping the malleable handle shaft to orient the active face to assume the selected orientation;

grasping the handle with the hand with the handle in the operative position;

positioning the active face against the anatomical tissue at the operative site while the handle is disposed at the location remote from the operative site;

emitting ultrasound energy from the ultrasound emitting member;

focusing the ultrasound energy at one or more focusing zones within a target area in the anatomical tissue and located a predetermined distance in front of the active face; and heating the tissue at the target area with the focused ultrasound energy to form a lesion.

22. The method of thermally ablating anatomical tissue as recited in claim 21 wherein said step of positioning includes introducing the handle shaft through an anatomical passageway of the patient to position the active face at the operative site while the proximal end of the handle shaft is disposed externally of the patient's body.

23. The method of thermally ablating anatomical tissue as recited in claim 22 wherein said step of manually shaping includes manually shaping the handle shaft for accommodation in the anatomical passageway.

24. The method of thermally ablating anatomical tissue as recited in claim 23 wherein said step of manually shaping includes manually shaping the handle shaft to assume a longitudinal configuration conforming to the longitudinal configuration of the anatomical passageway.

25. The method of thermally ablating anatomical tissue as recited in claim 21 wherein said step of manually shaping includes manually shaping the handle shaft to orient the active face to be disposed at a selected angle relative to the handle shaft.

26. The method of thermally ablating anatomical tissue as recited in claim 25 wherein said step of manually shaping includes manually shaping the handle shaft to orient the active face to face upwardly from the handle shaft.

27. The method of thermally ablating anatomical tissue as recited in claim 25 wherein said step of manually shaping includes manually shaping the handle shaft to orient the active face to face downwardly from the handle shaft.

28. The method of thermally ablating anatomical tissue as recited in claim 25 wherein said step of manually shaping includes manually shaping the handle shaft to orient the active face to face laterally from the handle shaft.

29. The method of thermally ablating anatomical tissue as recited in claim 21 and further including the step of manually reshaping the handle shaft so that the active face assumes another one of the plurality of different orientations with the handle in the operative position.

* * * * *